US010561793B2

(12) United States Patent
Finke et al.

(10) Patent No.: US 10,561,793 B2
(45) Date of Patent: Feb. 18, 2020

(54) SINGLE-USE DEVICE FOR INJECTION OF CARTRIDGE DRUGS

(71) Applicant: KPR U.S., LLC, Mansfield, MA (US)

(72) Inventors: Melvin A. Finke, Deland, FL (US); David L. Strader, Debary, FL (US); David R. Swisher, St. Charles, MO (US); Kathleen Tremblay, Westfield, MA (US)

(73) Assignee: KPR U.S., LLC, Mansfield, MA (US)

( * ) Notice: Subject to any disclaimer, the term of this patent is extended or adjusted under 35 U.S.C. 154(b) by 1131 days.

(21) Appl. No.: 14/481,303

(22) Filed: Sep. 9, 2014

(65) Prior Publication Data

US 2015/0073352 A1 Mar. 12, 2015

Related U.S. Application Data

(60) Provisional application No. 61/875,270, filed on Sep. 9, 2013.

(51) Int. Cl.
*A61M 5/24* (2006.01)
*A61L 2/00* (2006.01)
(Continued)

(52) U.S. Cl.
CPC .......... *A61M 5/2466* (2013.01); *A61L 2/0035* (2013.01); *A61L 2/0047* (2013.01);
(Continued)

(58) Field of Classification Search
CPC .......... A61M 2005/247; A61M 5/2466; A61M 5/3204; A61M 2005/2474;
(Continued)

(56) References Cited

U.S. PATENT DOCUMENTS 3,571,939 A    3/1971  Paul
3,783,997 A *  1/1974  Brown ................. A61M 5/002
                                                       206/365
(Continued)

FOREIGN PATENT DOCUMENTS

EP    0740942 A1   11/1996
EP    2457550 A1    5/2012
(Continued)

OTHER PUBLICATIONS

Office Action dated Oct. 25, 2016 in related Canadian Application No. 2923171, 3 pages.
(Continued)

*Primary Examiner* — Emily L Schmidt
(74) *Attorney, Agent, or Firm* — Arent Fox LLP

(57) ABSTRACT

The disclosed embodiment relates to an injection device that is a single patient use, disposable device containing a needle and a cartridge containing a drug, pharmaceutical product or other injectable agent. The device is initially provided in a pre-armed state in a first engagement configuration wherein the needle is separated from the septum of a cartridge. To arm the injection device, the professional urges the device from the first engagement or pre-armed configuration to a second engagement or armed configuration wherein the needle pierces the septum and provides a sterile fluid path to the drug, pharmaceutical product or other injectable agent contained within the cartridge. The disclosed embodiment is particularly adaptable to dental anesthetic applications, as well as other medical and veterinary applications.

29 Claims, 19 Drawing Sheets

(51) Int. Cl.
*A61M 5/32* (2006.01)
*A61M 5/34* (2006.01)
*B65B 5/04* (2006.01)

(52) U.S. Cl.
CPC .............. *A61M 5/3204* (2013.01); *A61M 5/34* (2013.01); *A61M 2005/2474* (2013.01); *B65B 5/04* (2013.01); *Y10T 29/4984* (2015.01)

(58) Field of Classification Search
CPC ................ A61M 5/31501; A61M 5/24; A61M 2005/2407; A61M 5/31571; A61M 2005/31508; A61M 5/31505; A61J 1/1406; A61J 1/062
See application file for complete search history.

(56) References Cited

U.S. PATENT DOCUMENTS

| | | | |
|---|---|---|---|
| 3,895,633 | A | 7/1975 | Bartner et al. |
| 4,309,388 | A | 1/1982 | Tenney et al. |
| 4,808,169 | A * | 2/1989 | Haber ............... A61M 5/24 604/110 |
| 4,834,717 | A | 5/1989 | Haber et al. |
| 4,860,643 | A | 8/1989 | Spearow |
| 4,910,942 | A | 3/1990 | Dunn et al. |
| 5,431,201 | A | 7/1995 | Torchia et al. |
| 5,478,321 | A | 12/1995 | Kimber |
| 5,695,477 | A | 12/1997 | Sfikas |
| 5,931,817 | A * | 8/1999 | Nguyen ............... A61M 5/002 604/192 |
| 5,997,513 | A | 12/1999 | Smith et al. |
| D608,886 | S | 1/2010 | Rueckert et al. |
| 8,034,034 | B2 | 10/2011 | Hess et al. |
| 8,152,763 | B2 | 4/2012 | Epperson |
| 8,852,158 | B1 | 10/2014 | Schaffer |
| 2001/0053886 | A1 | 12/2001 | Caizza |
| 2004/0241041 | A1 | 12/2004 | Woodworth et al. |
| 2006/0151714 | A1 | 7/2006 | Thilly et al. |
| 2006/0225809 | A1 | 10/2006 | Py et al. |
| 2007/0060897 | A1 | 3/2007 | Wang |
| 2007/0078408 | A1 | 4/2007 | Wang |
| 2007/0258851 | A1 | 11/2007 | Fogg et al. |
| 2007/0265579 | A1* | 11/2007 | Kleyman .......... A61M 5/31501 604/207 |
| 2008/0051729 | A1 | 2/2008 | Cheng |
| 2008/0181826 | A1 | 7/2008 | Windsheimer |
| 2008/0199353 | A1 | 8/2008 | Mlodzinski et al. |
| 2009/0137966 | A1 | 5/2009 | Rueckert |
| 2010/0005760 | A1 | 1/2010 | Matheyka |
| 2011/0092917 | A1* | 4/2011 | Wei ................. A61M 5/24 604/241 |
| 2012/0141322 | A1 | 6/2012 | Fogg |
| 2012/0141323 | A1 | 6/2012 | Fogg |
| 2013/0018311 | A1* | 1/2013 | Denning ............. A61M 5/2429 604/110 |
| 2015/0073353 | A1 | 3/2015 | Strader |
| 2016/0158101 | A1 | 6/2016 | Latiolais |

FOREIGN PATENT DOCUMENTS

| | | | |
|---|---|---|---|
| EP | 2540329 A1 | 1/2013 | |
| FR | 2250676 A1 | 6/1975 | |
| WO | 89/02760 A1 | 4/1989 | |
| WO | 2007/008257 A2 | 1/2007 | |
| WO | 2012/000554 A1 | 1/2012 | |
| WO | WO 2012000554 A1 * | 5/2012 | ............. A61M 5/28 |
| WO | 2013/063707 A1 | 5/2013 | |
| WO | 2013/134246 A1 | 9/2013 | |

OTHER PUBLICATIONS

International Preliminary Report on Patentability issed in International Application No. PCT/US2014/054765, dated Jun. 5, 2015.
International Search Report and Written Opinion issed in International Application No. PCT/US2014/054765, dated Nov. 24, 2014.
International Search Report and Written Opinion issed in International Application No. PCT/US2014/054775, dated Nov. 24, 2014.
Written Opinion of the International Preliminary Examining Authority issued in International Application No. PCT/US2014/054765, dated Mar. 12, 2015.
Written Opinion of the International Preliminary Examining Authority issued in International Application No. PCT/US2014/054775, dated Mar. 20, 2015.
Examination Report for European Patent Application No. 14771718.5, dated Aug. 21, 2018, 6 pages.
Office Action dated Oct. 3, 2017 in related U.S. Appl. No. 14/481,303, 14 pages.

* cited by examiner

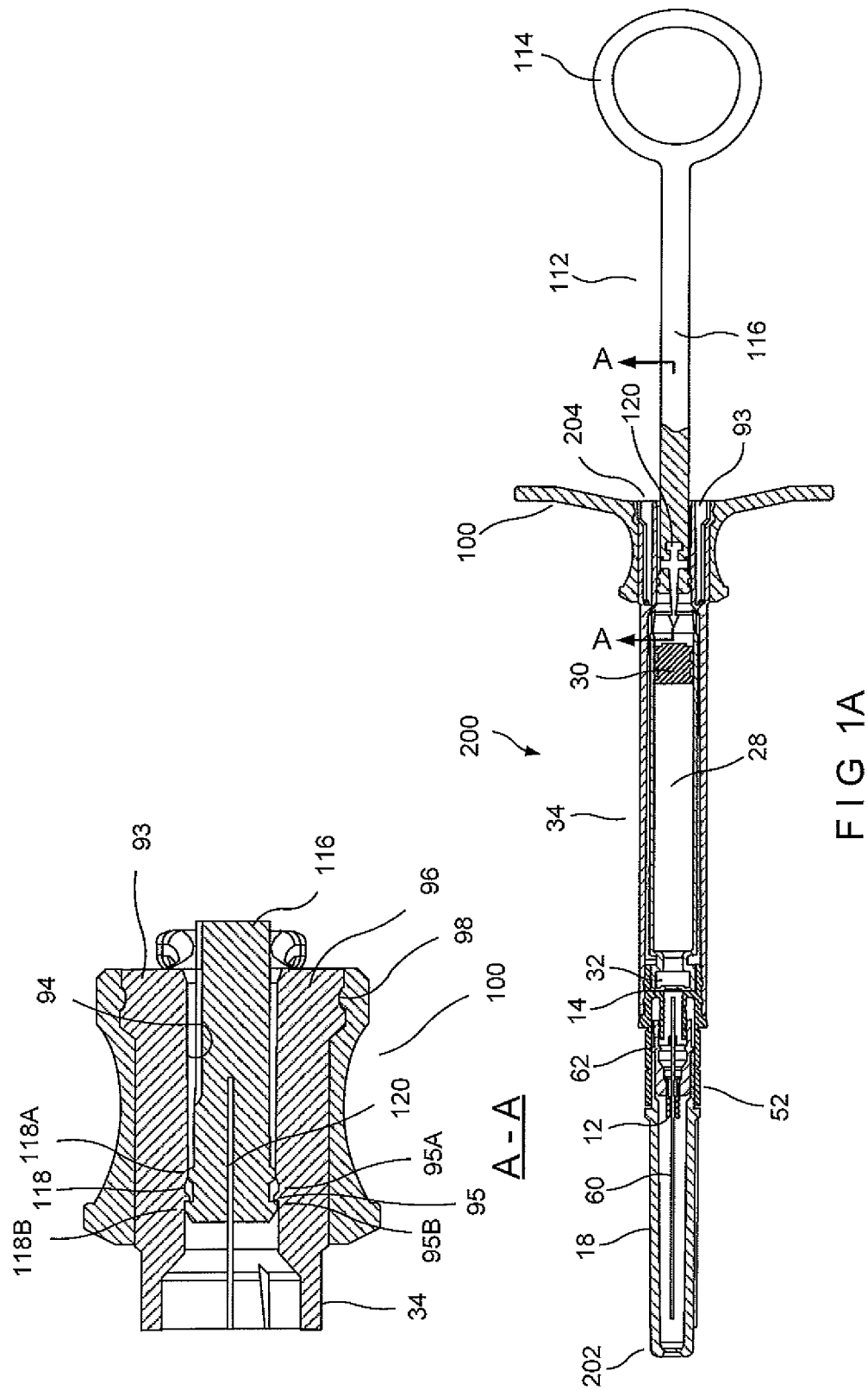

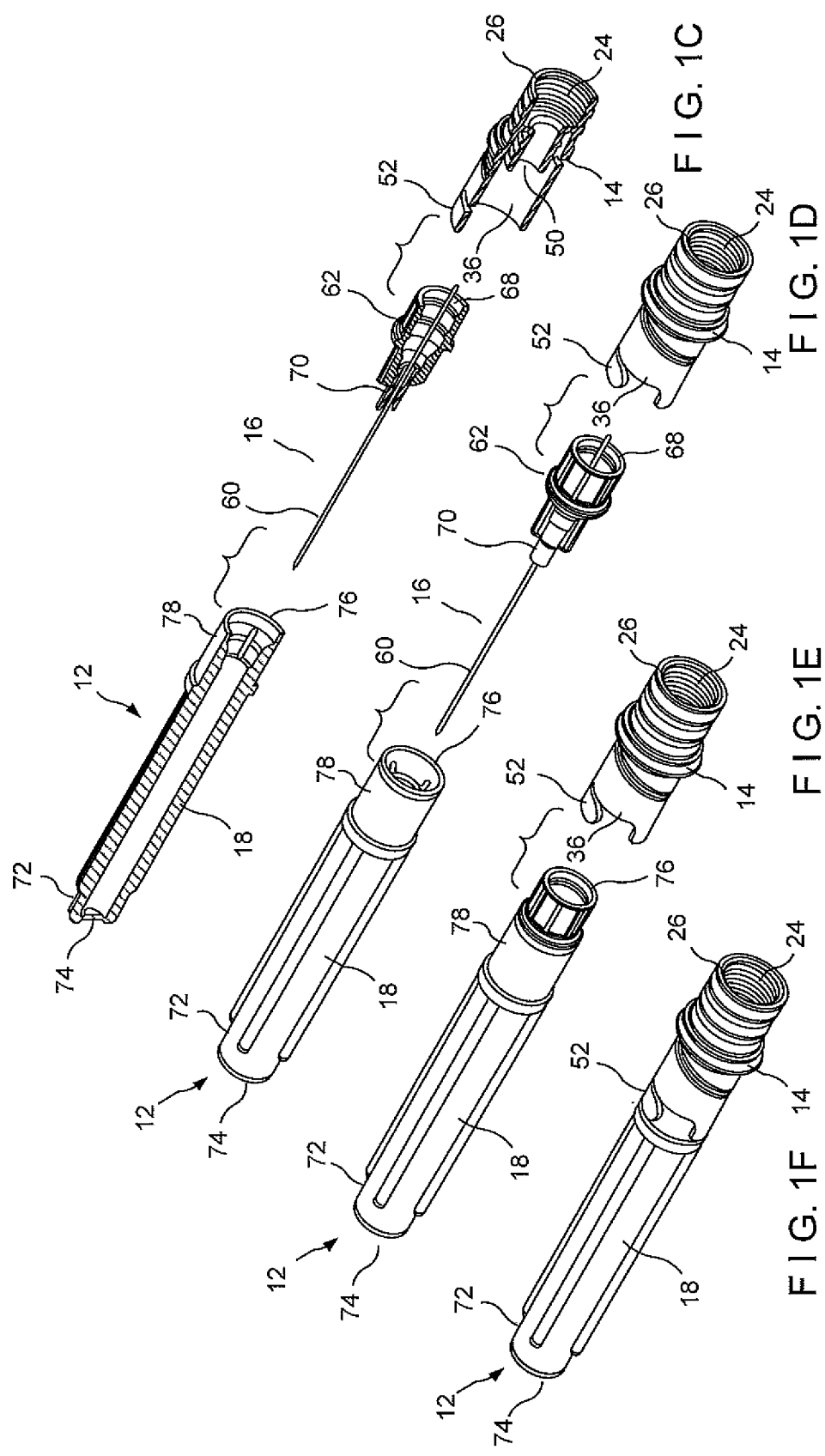

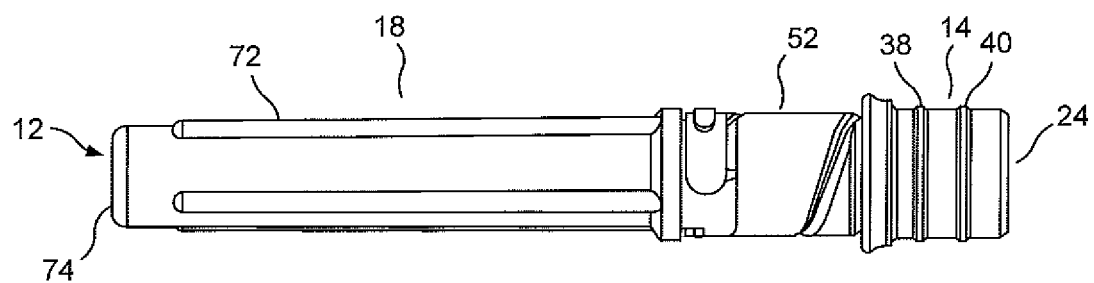
FIG. 3A
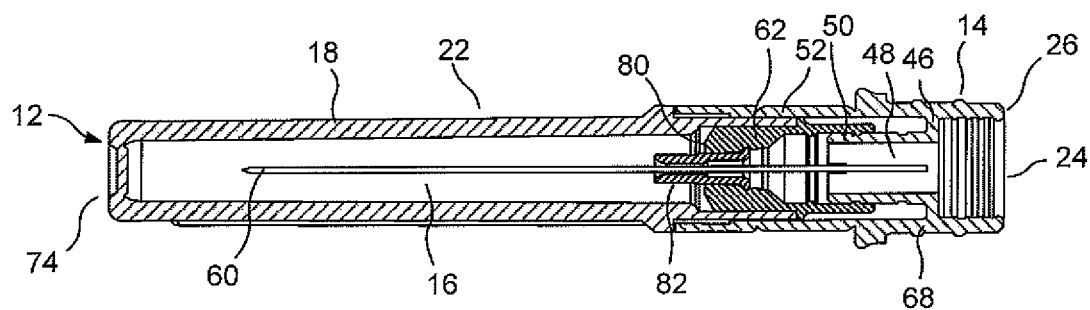
FIG. 3B
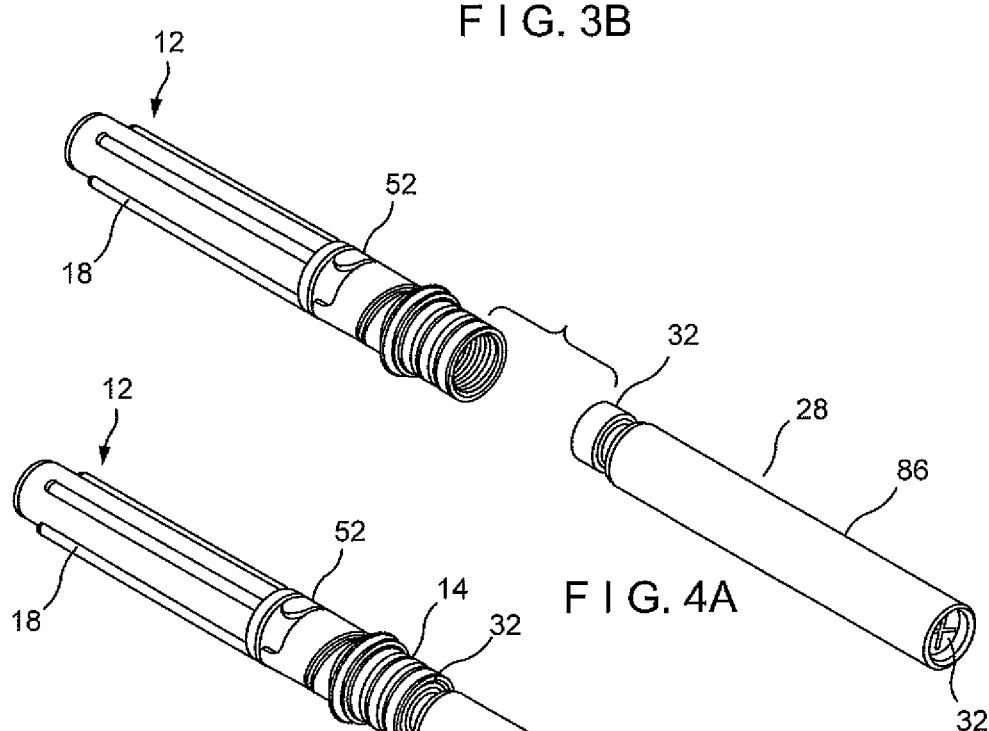
FIG. 4A
FIG. 4B

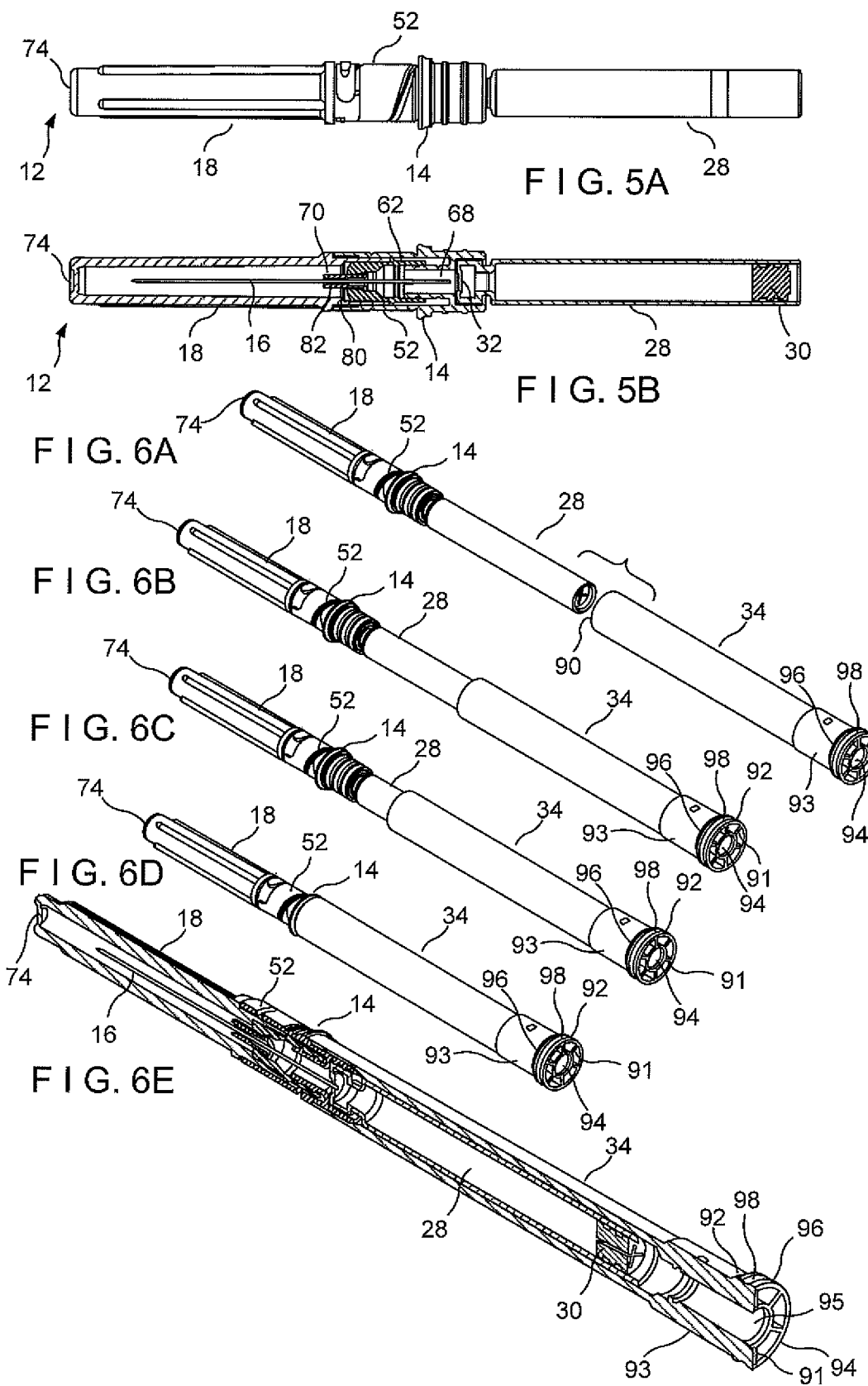

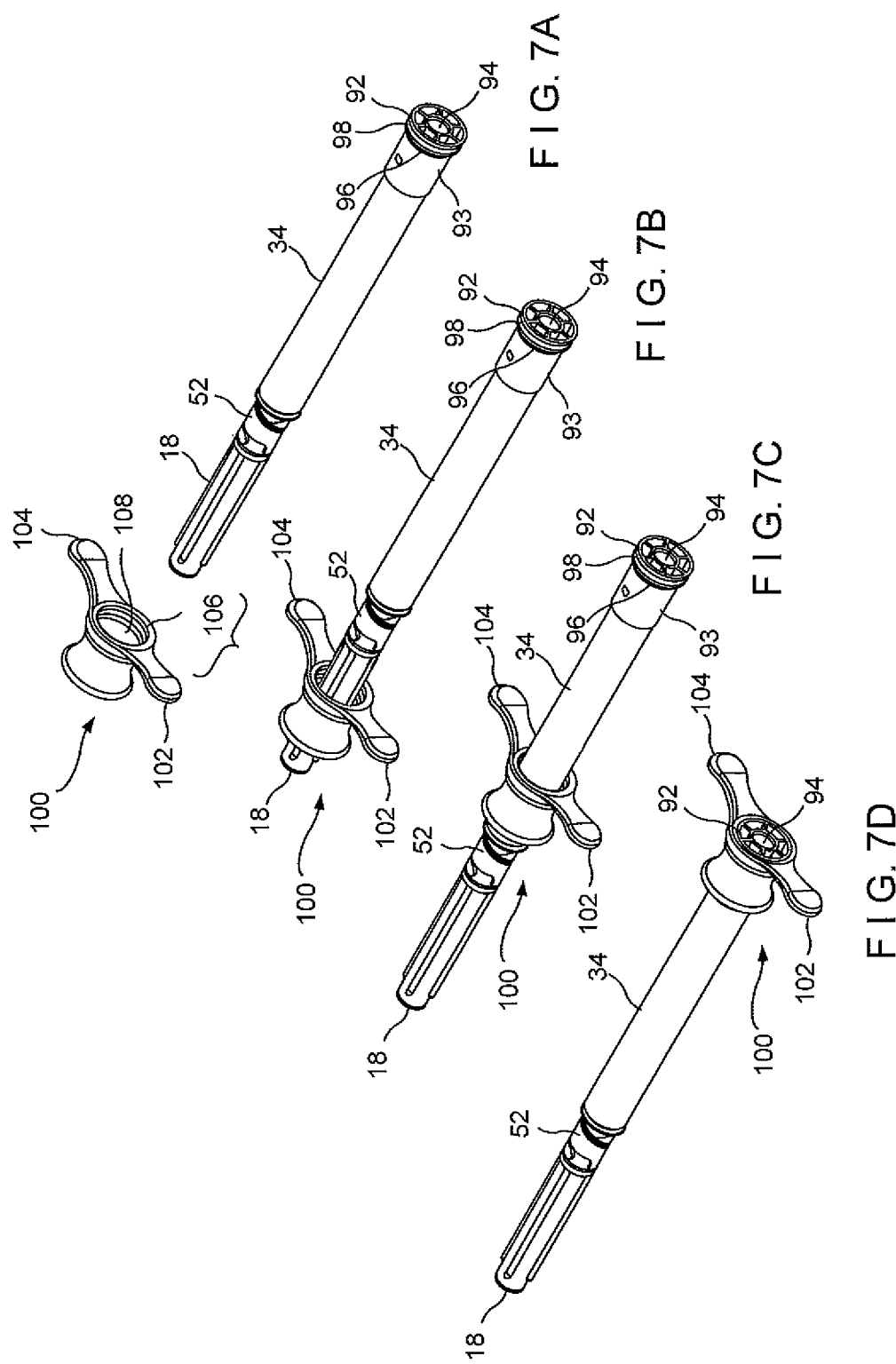

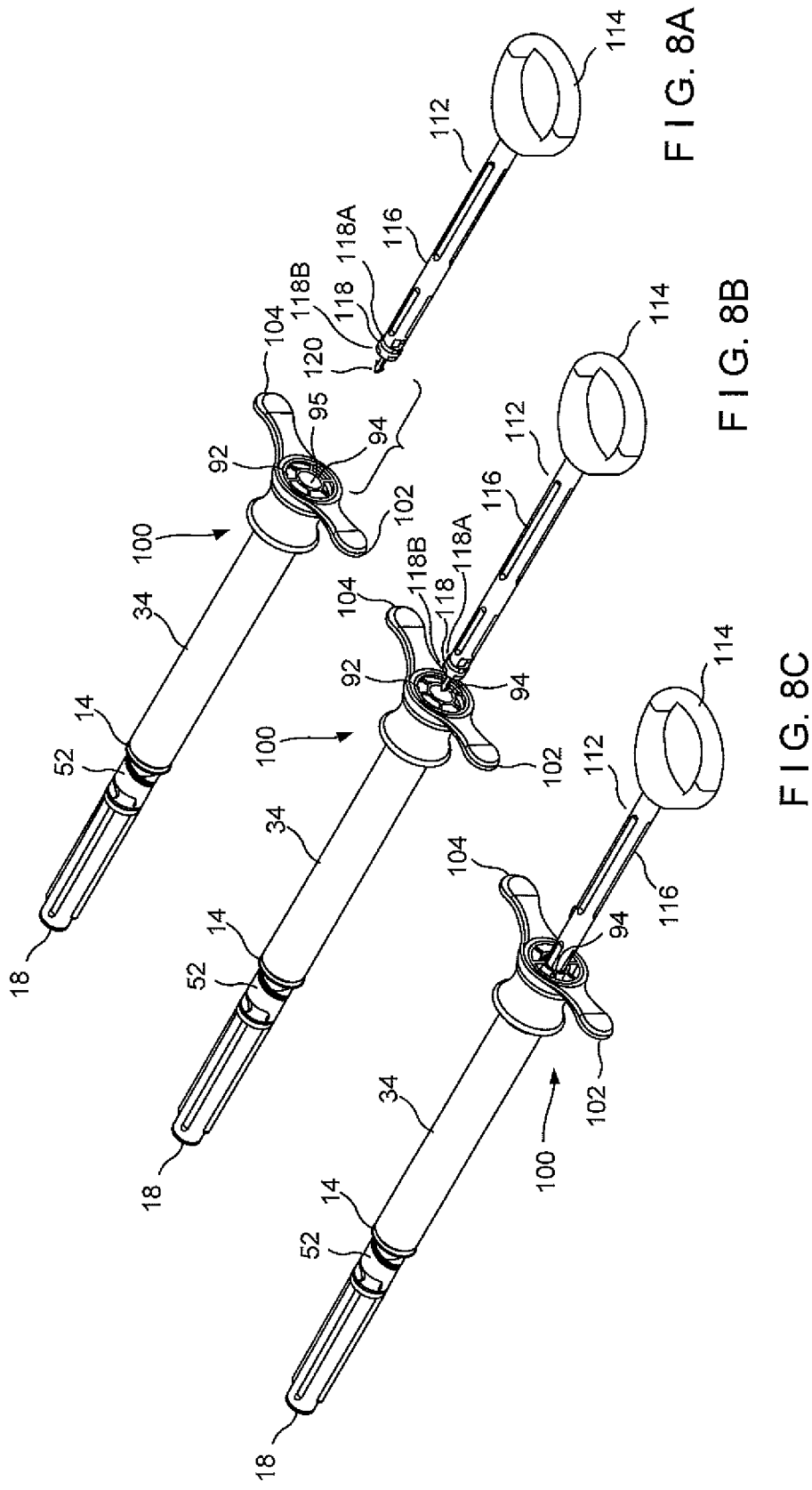

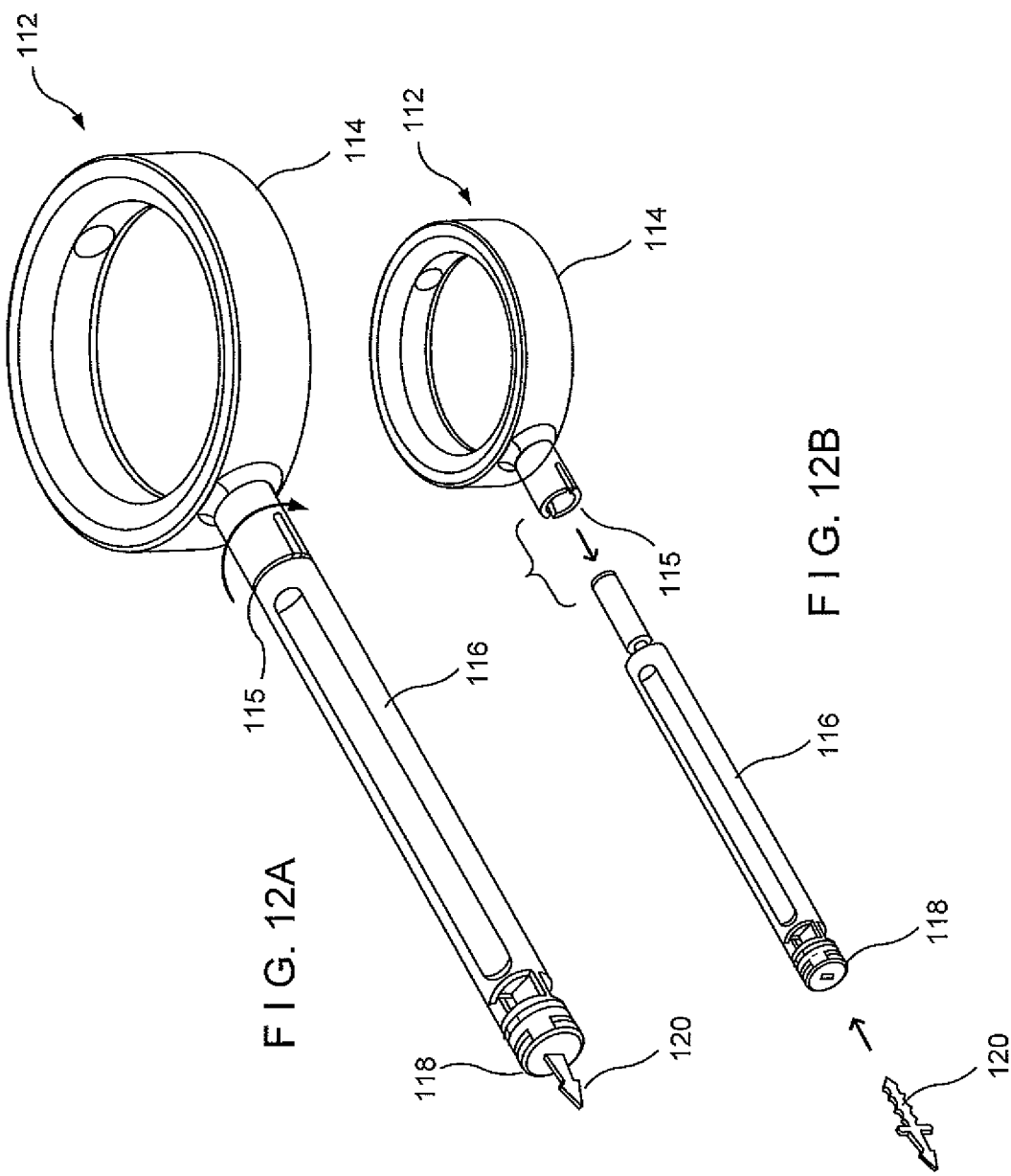

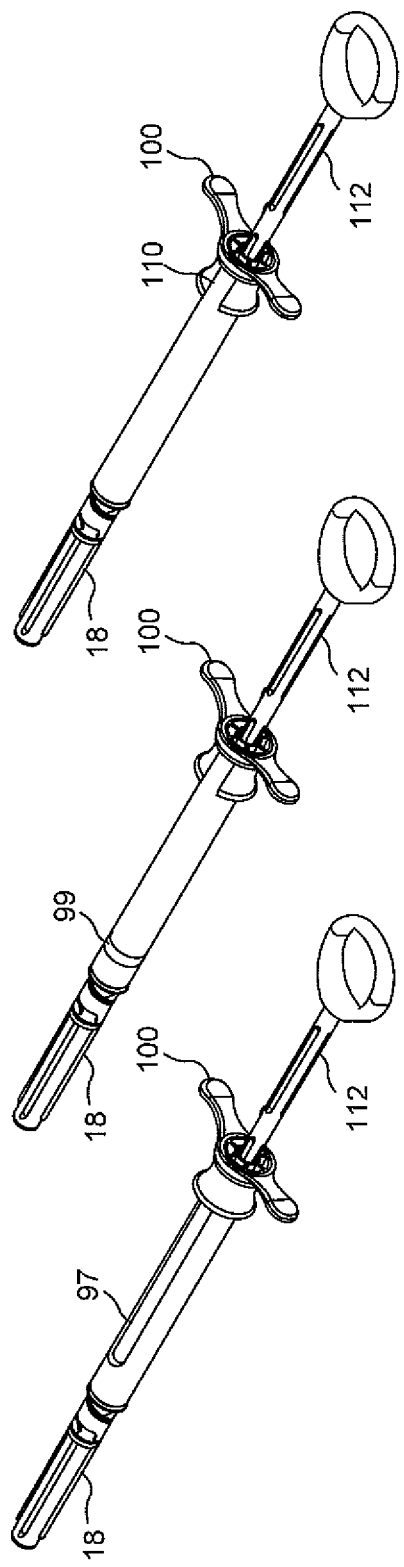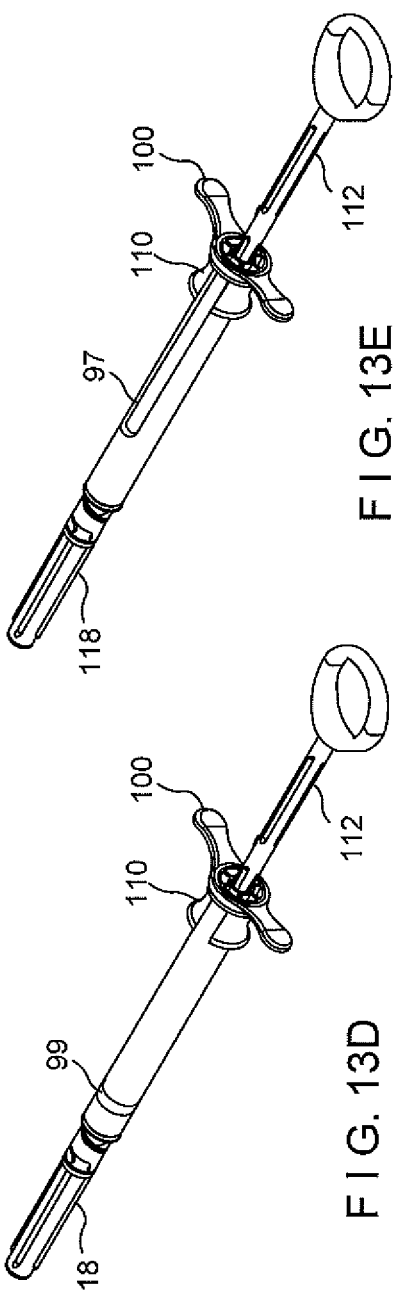

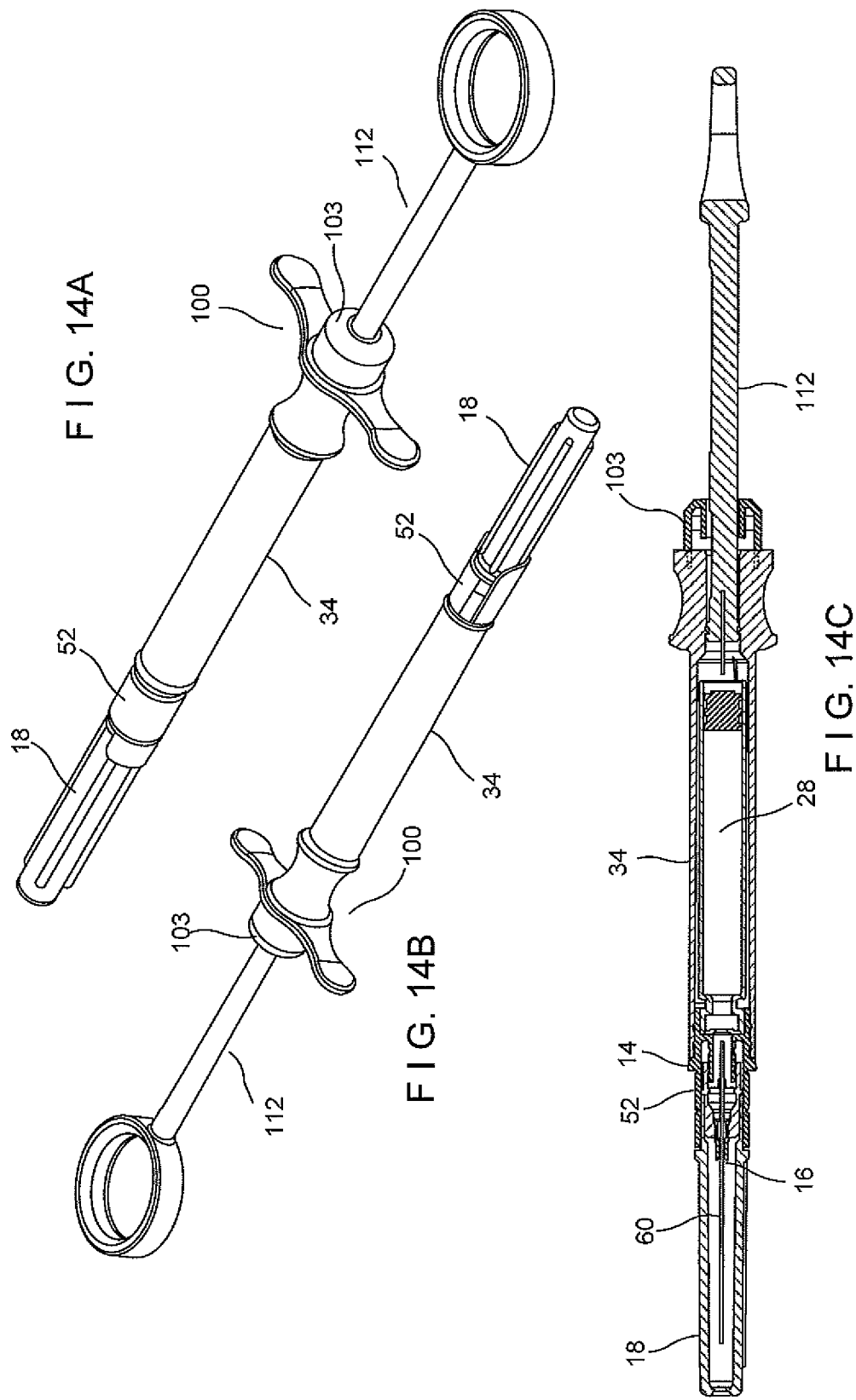

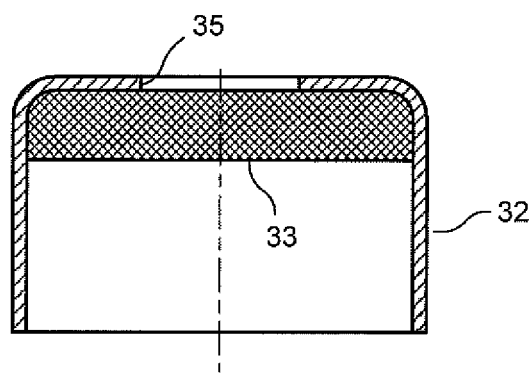
F I G. 15A
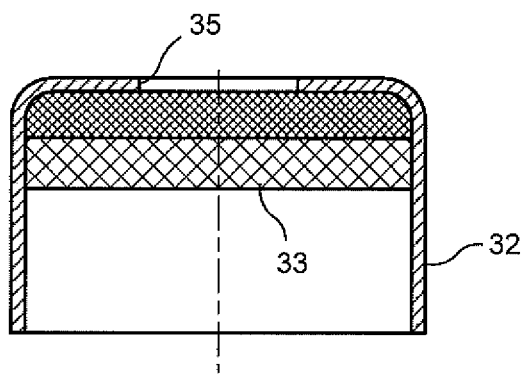
F I G. 15B

SINGLE-USE DEVICE FOR INJECTION OF CARTRIDGE DRUGS

This application claims priority under 35 U.S.C. 119(e) of U.S. Provisional Patent application Ser. No. 61/875,270, filed on Sep. 9, 2013, the disclosure of which is incorporated by reference herein in its entirety.

BACKGROUND

The present disclosure relates to a syringe or similar injection device, which is configured to inject an injectable agent, for example, a therapeutic agent, local anesthetic or other similar liquids from a cartridge, in a pre-loaded single-use configuration.

Conventionally, syringes for the sterile injection of injectable agents, such as, but not limited to, local anesthetics, therapeutic agents, cosmetic agents or other liquids, gels, or powders in the medical, dental or veterinary fields are filled with the injectable agent by a medical professional just prior to use. However, conventional prior art syringes may be problematic in that they may place the medical professional at a higher risk for an accidental needle stick due to the handling before and after the injection.

SUMMARY

It is therefore an object of the present disclosure to provide improvements in syringe-type injection devices, particularly pre-loaded single-use, disposable devices containing a needle and a cartridge containing drugs, pharmaceutical products, or other injectable agents.

It is therefore a further object of the present disclosure to provide improvements in syringe-type injection devices which are particularly adaptable to sterile injection of injectable agents, such as, but not limited to, local anesthetics, therapeutic agents, cosmetic agents or other liquids, gels, or powders in the medical, dental or veterinary fields.

These and other objects are attained by providing a sterile injector assembly, pre-loaded with a drug, pharmaceutical product or other injectable agent, such as, but not limited to, a local anesthetic. The sterile needle assembly includes a stainless steel cannula set within a hub with a needle sheath, bulk packaged and sterilized by gamma ray or ultra-violet irradiation or a similar process as appropriate to the design.

More particularly, taught herein is a disposable and sterile pre-loaded injection device comprising a cartridge with a closed first cartridge end and a second cartridge end including a cartridge plunger, a housing enclosing the cartridge, a needle hub holding a needle, and an adapter with a first adapter end and a second adapter end, the first adapter end slidably engaging the first cartridge end and a first housing end, and the second adapter end engaging the hub of the needle, wherein engagement of the second adapter end and the hub of the needle is movable between a first pre-armed configuration and a second armed configuration thereby creating a sterile fluid path for the injectable agent.

In order to use the device, the medical professional (which may include a dental, veterinary or similar professional) removes the device from the packaging, engages the plunger rod in some embodiments, removes a peel tab, engages or arms the needle so as to reconfigure the device from a pre-armed configuration to an armed configuration thereby puncturing the piercable septum of the cartridge with the butt end of the needle, removes the needle sheath, and proceeds to administer the drug, pharmaceutical product or other injectable agent to the patient. During the arming process, the cartridge remains fixed and stationary in the housing and a needle hub holding the needle is slidably disengaged from the first pre-armed configuration and moved in a proximal direction to slidably engage the second armed configuration thereby creating a sterile fluid path for the injectable agent.

BRIEF DESCRIPTION OF THE DRAWINGS

Further objects and advantages of the disclosure will become apparent from the following description and from the accompanying drawings, wherein:

FIG. 1A is a cross-sectional view of the assembled injection device of the present disclosure in the pre-armed configuration, including a cross-sectional area of detail along plane A-A.

FIG. 1C is a perspective exploded view, partially cut-away, illustrating the needle assembly of the present disclosure.

FIG. 1D is a perspective exploded view illustrating the needle assembly of the present disclosure.

FIG. 1E is a perspective partially exploded view, illustrating the needle assembly with the needle inserted into the needle sheath, of the present disclosure.

FIG. 1F is a perspective view, illustrating the needle assembly of the present disclosure.

FIG. 3A is a plan view, illustrating the needle assembly of the present disclosure.

FIG. 3B is a plan view, partially cut-away view, illustrating the needle assembly of the present disclosure.

FIG. 4A is a perspective, partially exploded view, illustrating the pre-armed cartridge assembly of the present disclosure.

FIG. 4B is a perspective view illustrated the pre-armed cartridge assembly of the present disclosure.

FIG. 5A is a plan view illustrating the pre-armed cartridge assembly of the present disclosure.

FIG. 5B is a perspective view, partially cut-away, illustrating the pre-armed cartridge assembly of the present disclosure.

FIG. 6A is a perspective, partially exploded view, illustrating the cartridge assembly of the present disclosure.

FIG. 6B is a first perspective view illustrating the insertion of the housing of the present disclosure.

FIG. 6C is a second perspective view illustrating the insertion of the housing of the present disclosure.

FIG. 6D is a perspective view illustrating the fully inserted housing, resulting in the cartridge assembly of the present disclosure.

FIG. 6E is a perspective view, partially cut-away, illustrating the cartridge assembly of the present disclosure.

FIG. 7A is a perspective view, illustrating the rotatable finger flange assembly exploded away from the cartridge assembly of the present disclosure.

FIG. 7B is a first perspective view illustrating the insertion of the cartridge assembly through the finger flange assembly of the present disclosure.

FIG. 7C is a second perspective view illustrating the insertion of the cartridge assembly through the finger flange assembly of the present disclosure.

FIG. 7D is a perspective view of the cartridge assembly with the finger flange assembly attached thereto in the present disclosure.

FIG. 8A is a perspective view, partially exploded, illustrating the plunger rod assembly with respect to the cartridge assembly with the finger flange of the present disclosure.

FIG. 8B is a perspective view illustrating the plunger rod attached to the housing of the present disclosure.

FIG. 8C is a perspective view illustrating the plunger rod inserted so that the harpoon engages the cartridge plunger.

FIG. 12A is a perspective view of an alternative embodiment of the plunger rod of the present disclosure.

FIG. 12B is a perspective exploded view of an alternative embodiment of the plunger rod of the present disclosure.

FIGS. 13A through 13E are perspective views illustrating further alternative embodiments of the present disclosure.

FIGS. 14A and 14B are first and second perspective views of a still further alternative embodiment of the present disclosure.

FIG. 14C is a plan, partially cut-away, view of the embodiment of FIGS. 14A and 14B of the present disclosure.

FIGS. 15A and 15B are cross-sectional views of the cap and septum of the present disclosure.

DETAILED DESCRIPTION

Figure 1B:
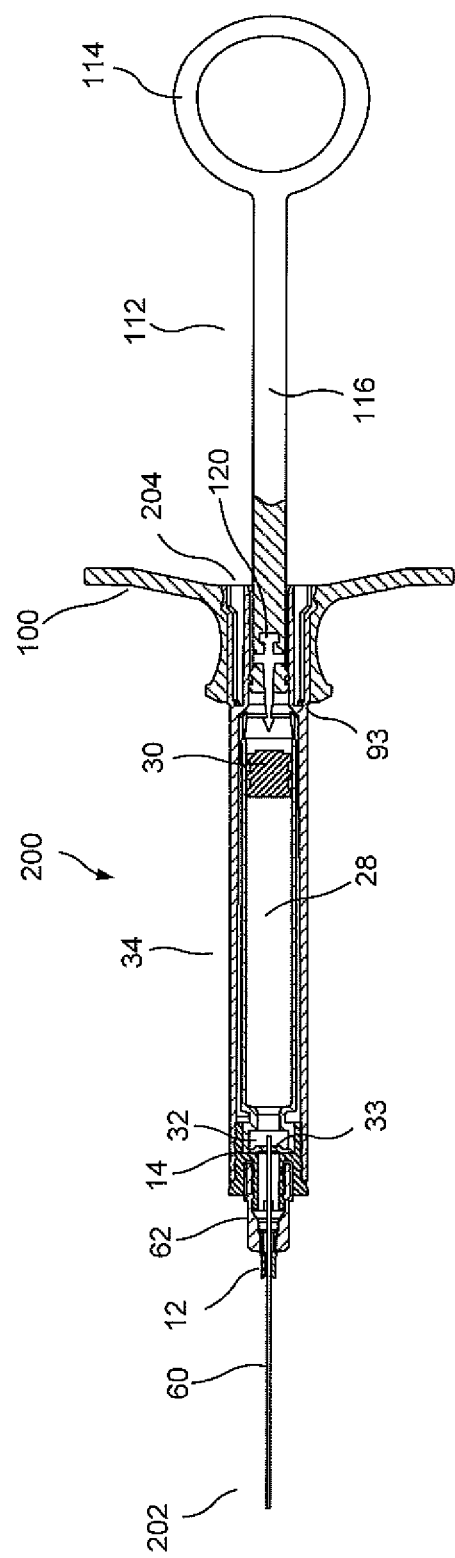
FIG. 1B is a cross-sectional view of the assembled injection device of the present disclosure in the armed configuration.

Disclosed herein are pre-loaded syringe assemblies and aseptic methods of manufacturing the same. The pre-loaded syringe assemblies include a plurality of sterility barriers to maintain the sterility of certain components of the syringe assemblies during packaging, shipping, storage until use by a medical professional.

Referring now to the drawings in detail wherein like numerals indicate like elements throughout the several views, one sees that the injection device 200 is a single-patient, single-use, disposable, sterile injection device pre-loaded with an injectable agent. As used herein, the term "injectable agent" refers to, but is not limited to, local anesthetics, therapeutic or pharmaceutical agents, cosmetic agents or other liquids, gels or powders in the medical, dental, veterinary or cosmetic fields. Further, one sees that FIG. 1A is a cross-sectional view of the fully assembled injection device 200, in a pre-armed state, with a cartridge 28 concentrically surrounded by housing 34. The cartridge 28 includes a cartridge plunger 30 on one end and a cap or band 32 that secures a piercable septum 33 thereto on the other end. The piercable septum 33 forms one sterility barrier to maintain sterility of the injectable agent held in the cartridge 28. A hub-to-cartridge interface 14 engages the cap 32 of the cartridge 28 as well as providing for two mounting positions for the hub 62 of needle assembly 12. In the first mounting position, which is illustrated in FIG. 1A, the injection device 200 is in its pre-armed state. A needle sheath 18 is mounted on the hub-to-cartridge interface 14, on the distal end 202 of the injection device 200, to shield the cannula 60 of needle assembly 12, and is held in position, so as to maintain the pre-armed state, by peel tab 52. Often, the harpoon 120 is visible through the housing, allowing the medical professional more visualization of the harpoon 120. Moreover, the length of housing 34 which provides for the visibility of the harpoon 120 further often provides for improved axial control of the injection device 200 during operation.

In the second mounting position, or armed state, which is illustrated in FIG. 1B, the injection device 200 is in its armed state with the cannula 60 penetrating the piercable septum 33 held in place by the cap 32 thereby creating a sterile fluid path for the injectable agent.

The interaction and interface of the needle sheath 18 with the peel tab 52 at location 122 forms another sterility barrier to maintain the sterility of the cannula 60 during packing, shipping and storage until the peel tab 52 is disengaged by the medical professional. The sterility barrier 122 extends circumferentially about the needle sheath 18. The peel tab 52 can be formed as a removable band at a terminal end of the hub-to-cartridge interface 14. Another sterility barrier 124 is formed by the interaction and interface of the hub-cartridge interface 14 and the housing 34. The sterility barrier 126 extends circumferentially about the hub-to-cartridge interface 14 to maintain sterility of a butt end 68 of cannula 60 during packing, shipping and storage until use by a medical professional.

Finger flange assembly 100 is mounted on the housing 34 at the proximal end 204 of the injection device 200. In some embodiments, the finger flange assembly 100 is rotatable about the housing 34. The plunger rod assembly 112 includes a thumb ring 114 and a shaft 116 which further includes a harpoon 120 which engages the cartridge plunger 30 of the cartridge 28.

Figure 2:
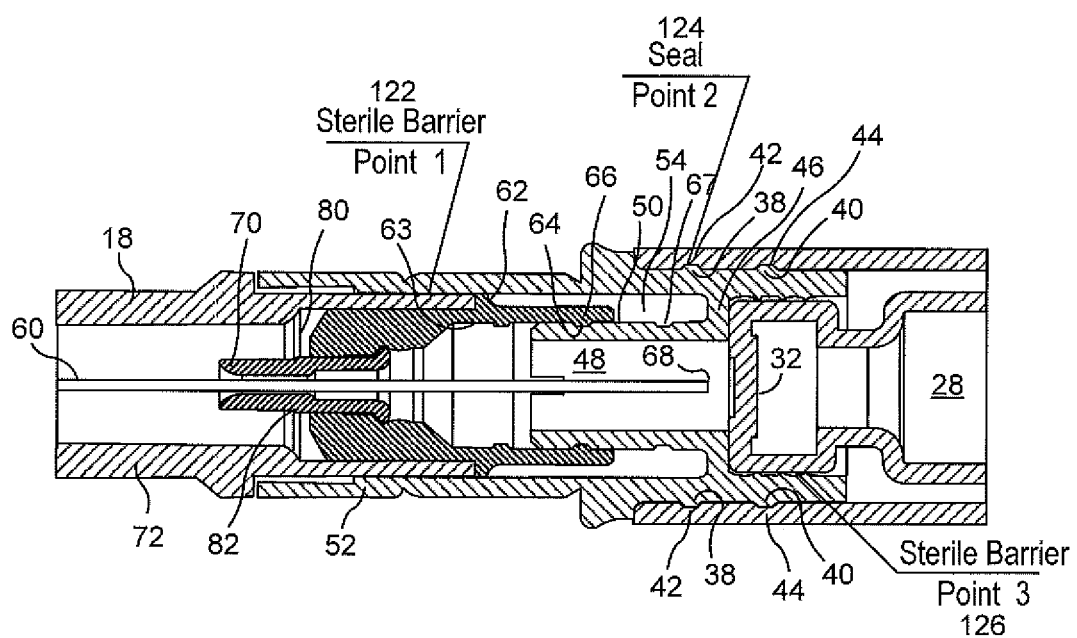
FIG. 2 is a cross-sectional view illustrating sterile barrier points of the cartridge assembly of the present disclosure.

FIGS. 1C-1F illustrate the components of the needle assembly 12, including a hub-to-cartridge interface (or adapter) 14, a needle 16 and the needle sheath 18. FIGS. 2 and 3B illustrate cross-sectional details of these elements. Manufacturing of the injection device 200 involves the construction of the needle assembly 12.

The hub-to-cartridge interface 14 is formed from polyethylene or polypropylene, but is not limited thereto, and is intended to provide one or more sterility barriers, tamper evidence, and connectivity of the various elements. Hub-to-cartridge interface 14 includes a first open circular end 24 formed by circular wall 26 wherein, as shown in detail in FIG. 2, the exterior of circular wall 26 includes two outwardly extending annular ridges 38, 40. A transverse annular wall 46 is formed inwardly from first open circular end 24. Transverse annular wall 46 further includes a central passageway 48. Interior cylindrical needle mount wall 50 extends from the periphery of central passageway 48 toward the second open circular end 36 of the hub-to-cartridge interface 14 and provides a mount for the needle 16. Hub-to-cartridge interface 14 further includes a pliable plastic peel band or tab 52 formed of low density polyethylene, but not limited thereto, which maintains and engages the needle sheath 18 thereby forming a sterile barrier and further maintaining the needle 16 in the first configuration prior to the arming of the injection device 200. The peel tab 52 further provides a tamper indicator to indicate if there has been any tampering with the injection device 200.

The needle 16 is formed from aluminum, but is not limited thereto, and includes a conventional cannula 60 as well as a hub 62 (hub 62 may likewise be formed from polyethylene or polypropylene) which, as shown in FIG. 2, is outwardly concentric from the interior cylindrical needle mount wall 50 of the hub-to-cartridge interface 14 and forms one of two engagement positions therewith, for example, a first engagement position corresponds to the "pre-armed" state and a second engagement position corresponds to the "armed" state. In some embodiments, first engagement position can be a first detent engagement position that corresponds to the "pre-armed" state and the second engagement position can be a second detent position that corresponds to the "armed" state. The first engagement configuration is formed by the inwardly extending annular ridge 64 on the interior cylindrical wall 63 of the hub 62 engaging the first inwardly extending annular notch 66 on the exterior of the interior cylindrical needle mount wall 50. The second engagement configuration is formed by the inwardly extending annular ridge 64 on the interior cylindrical wall 63 of the hub 62 engaging the second inwardly extending annular notch 67 (illustrated in FIG. 2 as being to the right of first inwardly extending annular notch 66) on the exterior of the interior cylindrical needle mount wall 50.

In other words, when the inwardly extending annular ridge 64 formed on the interior of the interior cylindrical wall of the hub 62 is engaged, for example, detent engage, with the first inwardly extending annular notch 66, the injection device 200 is in a first configuration in a pre-armed state. However, when the inwardly extending annular ridge 64 formed on the interior of the interior cylindrical wall of the hub 62 is engaged, for example, detent engaged with the second inwardly extending annular notch 67, the injection device 200 is in a second configuration in an armed state. It is envisioned that different embodiments of this disclosure could implement the first and second engagement configurations (e.g., the pre-armed and armed configurations, respectively) in many different equivalent structures.

Hub 62 further includes an insert 70 at the initial joining of the hub 62 and the cannula 60. In the pre-armed configuration of FIG. 2, the butt end 68 of the needle 16 is positioned within the central passageway 48.

The sheath 18 includes generally cylindrical wall 72 with a closed end 74 and an open end 76. The sheath 18 is formed from polyethylene or polypropylene, but is not limited thereto. The exterior portion of cylindrical wall 72 has an area 78 of reduced outer diameter in which pliable plastic peel tab 52 of hub-to-cartridge interface 14 is circumferentially positioned thereby allowing the sheath 18 to be mounted on the injection device 200. Additionally, interior transverse wall 80 is formed within the interior of sheath 18, inwardly adjacent from open end 76. Annular passageway 82 is formed within interior transverse wall 80, through which hub 62 of needle 16 is seated and through which insert 70 protrudes.

FIGS. 1C, 1D and 1E depict the insertion and axial relationship of the cannula 60 of needle 16 into the open end 76 of sheath 18 so that hub 62 protrudes from open end 76 of sheath 18. As shown in FIG. 2, hub 26 is seated in annular passageway 82 of interior transverse wall 80 with insert 70 protruding therethrough.

FIGS. 1E, 1F, 3A and 3B depict the insertion of and the axial relationship of the hub-to-cartridge interface 14 onto the hub 62 of needle 16 and the sheath 18 so that, as shown in FIG. 2, the inwardly extending annular ridge 64 on the interior cylindrical wall of hub 62 of needle 16 engages with the first inwardly extending annular notch 66 on the exterior of the interior cylindrical needle mount wall 50 of hub-to-cartridge interface 14. Further, the pliable plastic peel tab 52 is positioned within area 78 of reduced diameter on cylindrical wall 72 of sheath 18 thereby forming the needle assembly 12 as shown in FIGS. 1F, 3A and 3B.

FIGS. 4A, 4B, 5A and 5B depict the insertion and axial relationship of the cartridge 28 and the hub-to-cartridge interface 14. Cartridge 28, which may be a drug carpule, includes glass cylindrical walls 86 forming a storage volume for the drug, pharmaceutical product or other injectable agent, such as, but not limited to, a dental anesthetic. The cartridge 28 includes a cartridge plunger 30 at one end and a cap 32 at the other end. As shown in FIGS. 15A and 15B, the cap 32 holds a piercable septum 33 in place (FIG. 15A discloses a single layer septum 33 while FIG. 15B discloses a dual layer septum 33), exposed through opening 35 in the cap 32. The needle assembly 12 (which has been bulk sterilized by gamma ray, ultra-violet or a similar method) and cartridge 28 are brought into a controlled area (laminar airflow ISO class air supply), The cartridge 28 is oriented vertically with the cap 32, for example, an aluminum band or cap, on top and its top surface is sterilized with pulsed ultra-violet light, gamma rays, or by a similar method. The needle assembly 12 is then pressed onto the cap 32 as shown in FIGS. 2, 4B, 5A and 5B whereby the interior of circular wall 26 of the hub-to-cartridge interface 14 forms a friction fit with the cap 32 of cartridge 28, with the transverse annular wall 46 of the hub-to-cartridge interface 14 providing a maximum insertion, and a seat for the cartridge 28, thereby "pre-arming" the cartridge 28 in that the butt end 68 of the needle 16 has access to the cap 32 of the cartridge 28 (but is separated therefrom) through central passageway 48 in transverse annular wall 46 of the hub-to-cartridge interface 14. Additionally, the hub-to-cartridge interface 14 maintains a sterile barrier around the cap 32 and holds the assembly in position.

FIGS. 6A-6E depict the attachment and axial relationship of the housing 34 to the cartridge 28 and the hub-to-cartridge interface 14. Housing 34 is formed from injection molded clear plastic (but is not limited thereto) to allow for drug identification and visual confirmation of aspiration. The housing 34 often has no sterility requirement. Housing 34 is cylindrical with a first open end 90 with inwardly extending annular notches 42, 44 on the interior of housing 34, inwardly adjacent from first open end 90. Housing 34 further includes second open end 92, with a mounting hub 93 of somewhat increased diameter and a passageway 94 of reduced diameter passing therethrough for receiving the plunger rod assembly 112 as shown in FIGS. 8A-8C. Mounting hub 93 further includes radially oriented internal fins 91 between the interior wall of mounting hub 93 and the exterior wall of passageway 94. Mounting hub 93 further includes an annular lip 96 with an annular groove 98 formed thereon for mounting or rotatably engaging the finger flange assembly 100 (see the area of cross-sectional detail of FIG. 1A as well as FIGS. 7A-7D and 8A-8C). An internal annular retention ring 95 is formed on the interior of passageway 94 for engaging with a corresponding external annular retention channel (see element 118, FIG. 8A) on the plunger rod assembly 112. The internal annular retention ring 95 has a cross section with a sloped surface 95A facing toward the proximal end or user end, in order to facilitate insertion of the plunger rod assembly 112, but with an abrupt orthogonal surface 95B toward the distal end in order to capture the plunger rod assembly 112 once it is inserted, and to resist any subsequent withdrawal of the plunger rod assembly 112. The annular retention channel 118 is formed on shaft 116 of plunger rod assembly 112 between annular ring 118A and distal annular terminating ridge 118B. When the shaft 116 of plunger rod assembly 112 is initially inserted into passageway 94, the distal end of plunger rod assembly 116 slides over the sloped surface 95A of internal annular retention ring 95 so that internal annular retention ring 95 is captured within annular retention channel 118 between annular ring 118A and distal annular terminating ridge 118B. Similarly, the relationship or contact between the opposing orthogonal surfaces of distal annular terminating ridge 118B and orthogonal surface 95B resists any subsequent withdrawal of the plunger rod assembly 112 from the passageway 94. Likewise, the relationship or contact between the sloped surface 95A of internal annular retention ring 95 and the annular ring 118A causes a snap detent engagement of the plunger rod assembly 112 which holds the plunger rod assembly 112 in place, but which allows the medical professional to press against the plunger rod assembly 112 to overcome the snap detent engagement, thereby often causing both audible and tactile feedback, with the plunger rod assembly 112 being driven into passageway 94.

Alternative embodiments of housing 34 include a transparent view port 97 as shown in FIG. 13A to provide a direct line of sight to the cartridge 28, and likewise may include a magnification bubble 99 as shown in FIGS. 13B and 13D to provide enhanced acuity as to the cartridge aspiration. As shown in the transition from FIG. 6A through FIG. 6D, which may be performed outside of the laminar airflow ISO class air supply, the end of the cartridge 28 with the cartridge plunger 30 is inserted into the first open end 90 of the housing 34. The cartridge 28 is inserted further into the housing 34 until the housing 34 reaches hub-to-cartridge interface 14 and the inwardly extending annular notches 42, 44 on the interior of housing 34 can engage, for example, detent engage with two outwardly extending annular ridges 38, 40 of hub-to-cartridge interface 14 thereby resulting in the configuration shown in FIGS. 2, 6D and 6E and further resulting in a seal point and a sterile barrier between the housing 34 and the hub-to-cartridge interface 14.

With reference to FIGS. 7A-7D, the axial relationship and attachment of the rotatable finger flange assembly 100 to housing 34 is depicted. Rotatable finger flange assembly 100 is formed from injection molded plastic, but is not limited thereto, and often has no sterility requirement. Rotatable finger flange assembly 100 has two finger flanges 102, 104 for use by the medical professional during injection and further has a central bore 106 with an internal annular ridge 108 for engaging annular groove 98 of annular lip 96 of mounting hub 93 of housing 34 thereby providing for a snap fit with rotatable engagement between the finger flange assembly 100 and the housing 34 which allows the user or medical professional to orient the bevel of the needle 16 during use. Bevel orientation can be achieved in other ways, such as, but not limited to, a fixed finger flange assembly in combination with either a rotating plunger rod or a plunger rod with a rotating harpoon. Alternative embodiments of the finger flange assembly 100 are shown in FIGS. 13C and 13D wherein the finger flange assembly 100 further includes notches 110 to allow the finger flange assembly 100 to be opaque plastic while providing the professional the ability to read the cartridge information in some embodiments and in FIGS. 14A, 14B and 14C wherein the finger flange assembly 100 is integral with the housing 34 and a non-removable plunger cap 103 is provided. As shown in the progression from FIG. 7A through 7D, the closed end 74 of the sheath 18 is inserted into central bore 106 of rotatable finger flange assembly 100 and the rotatable finger flange assembly 100 is moved to annular groove 98 on annular lip 96 on mounting hub 93 of housing 34 to form a snap fit with rotatable engagement thereto thereby resulting in the configuration shown in FIG. 7D.

Figure 18:
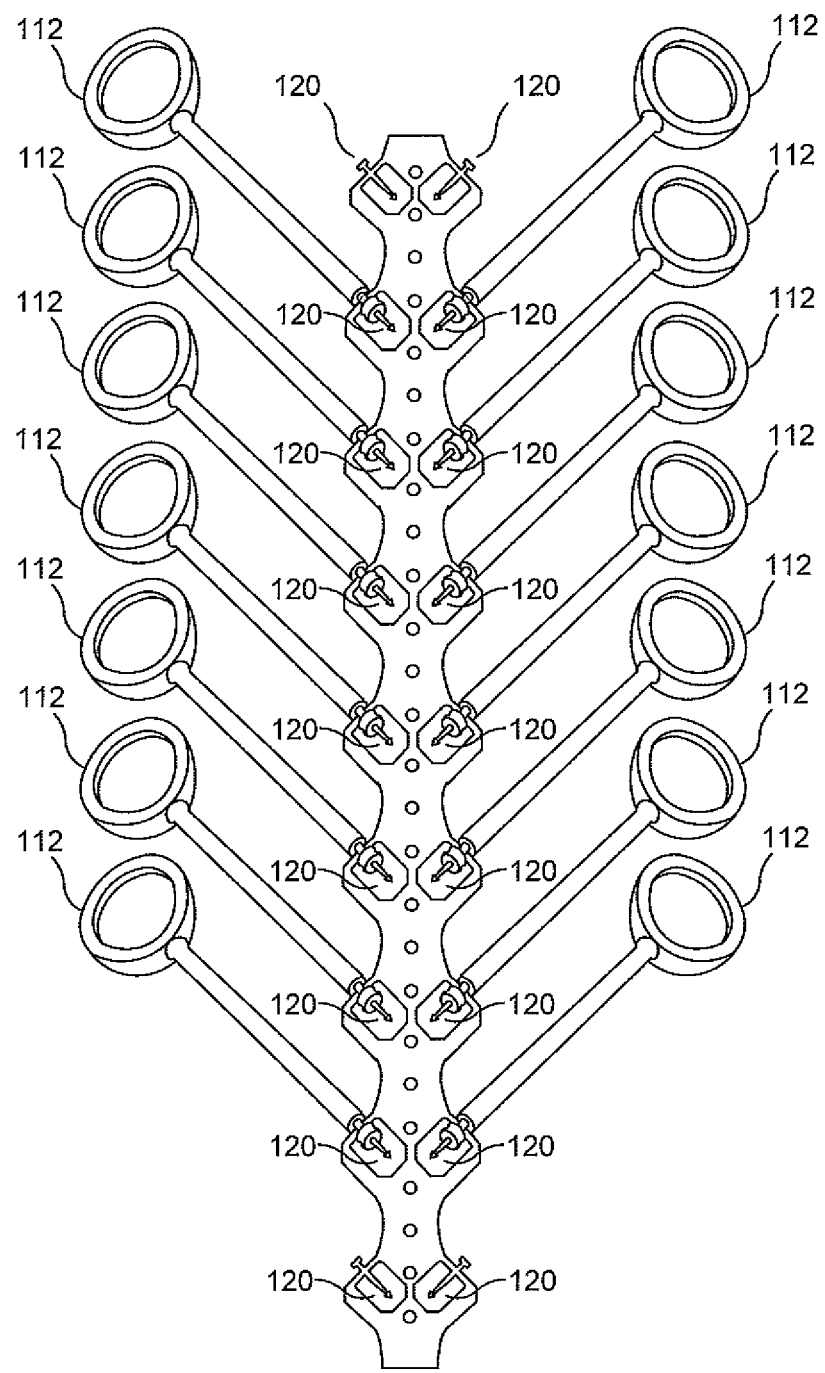
FIG. 18 is a diagram of a plunger assembly strip which may be used in the assembly of an embodiment of the present disclosure.

With reference to FIGS. 8A, 8B and 8C, the structure and axial relationship of the plunger rod assembly 112 to the housing 34 is depicted. The plunger rod assembly 112 includes a hollow circular thumb ring 114 attached to a shaft 116. The shaft 116 terminates in an external annular retention channel 118 and a longitudinally extending harpoon 120. The assembly of the harpoon 120 into the shaft 116 can be done in many different ways. For example, as depicted in FIG. 12B the harpoon 120 may be press fit into a terminal end of the shaft 116. In another example depicted in FIG. 18 the harpoon 120 is insert molded as part of molding the shaft 116.

An alternative plunger rod assembly 112 is illustrated in FIGS. 12A and 12B, which includes a swivel configuration 115 between the hollow circular thumb ring 114 and the shaft 116. The plunger rod assembly 112 is inserted into passageway 94 of housing 34 so that external annular retention channel 118 engages with internal annular retention ring 95 of housing 34 as shown in FIG. 8B. This snap-fit engagement maintains the plunger rod assembly 112 connected to the housing 34 while maintaining the longitudinally extending harpoon 120 from contacting the cartridge plunger 30, and further often maintaining the harpoon 120 in a location visible to the medical professional through the housing 34. As described below, when the professional is ready to operate the injection device 200, the medical professional can press the plunger rod assembly 112 to overcome this engagement and to urge the longitudinally extending harpoon 120 against the cartridge plunger 30 of cartridge 28 so that harpoon 120 engages, for example, detent engages the cartridge plunger 30 of cartridge 28 as shown in FIG. 8C. Alternatively, the plunger rod assembly 112 may be packaged with, but be separate from, the apparatus of FIG. 7D, wherein the medical professional would insert the plunger rod assembly 112 prior to use.

Figure 17:
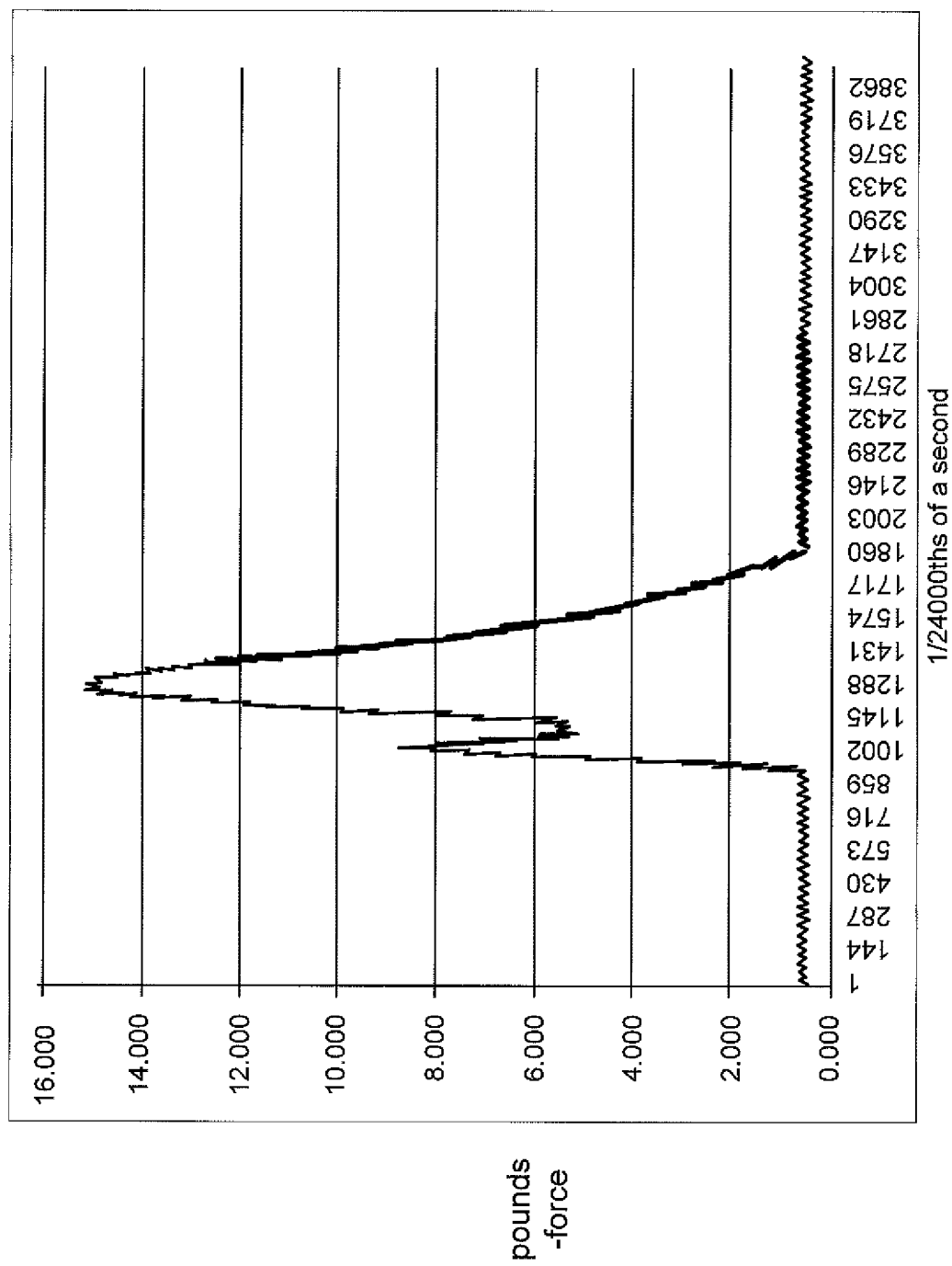
FIG. 17 is a chart of force versus time for a thumb ring and plunger of an embodiment of the present disclosure.

This configuration of the external annular channel 118 and the internal annular retention ring 95 often provides a tactile snap, as well as audible feedback, for the user while pushing the plunger rod assembly 112 to operate the injection device 200. FIG. 17 illustrates that as force or energy is applied, the snap detent configuration of internal annular retention ring 95 and external annular channel 118 holds the energy until approximately fifteen pounds-force is applied, as shown on the Y-axis, whereas the X-axis is sample number, at a sampling rate of 24,000 samples per second. Then, disengagement of the detent configuration occurs, the momentum is momentarily released to allow the harpoon 120 to travel at a faster speed and force than would occur without the snap detent configuration. This is particularly a benefit for users who are not as likely to use an aggressive slap style of activation.

An example embodiment of injection device 200 frequently includes packaging in a flow wrap or similar package (not shown) as a clean barrier. As mentioned previously, this packaging may include the plunger rod assembly 112 separated from the remainder of the injection device 200.

Figure 19:
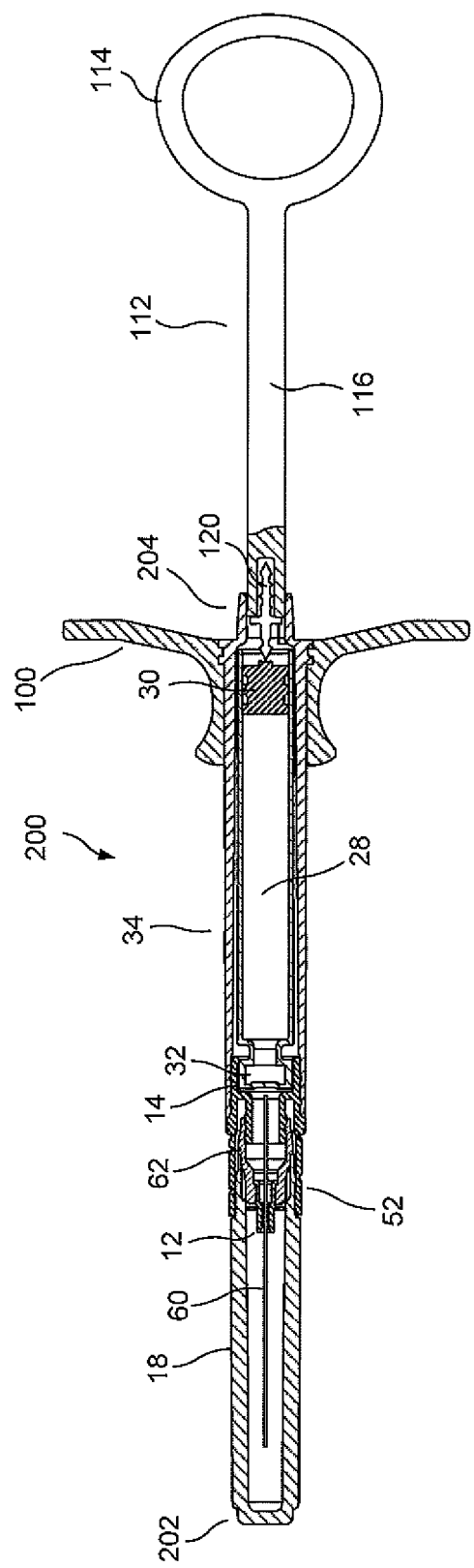
FIG. 19 is a cross-sectional view of an alternative embodiment of the assembled injection device of the present disclosure in the pre-armed configuration.
Figure 20:
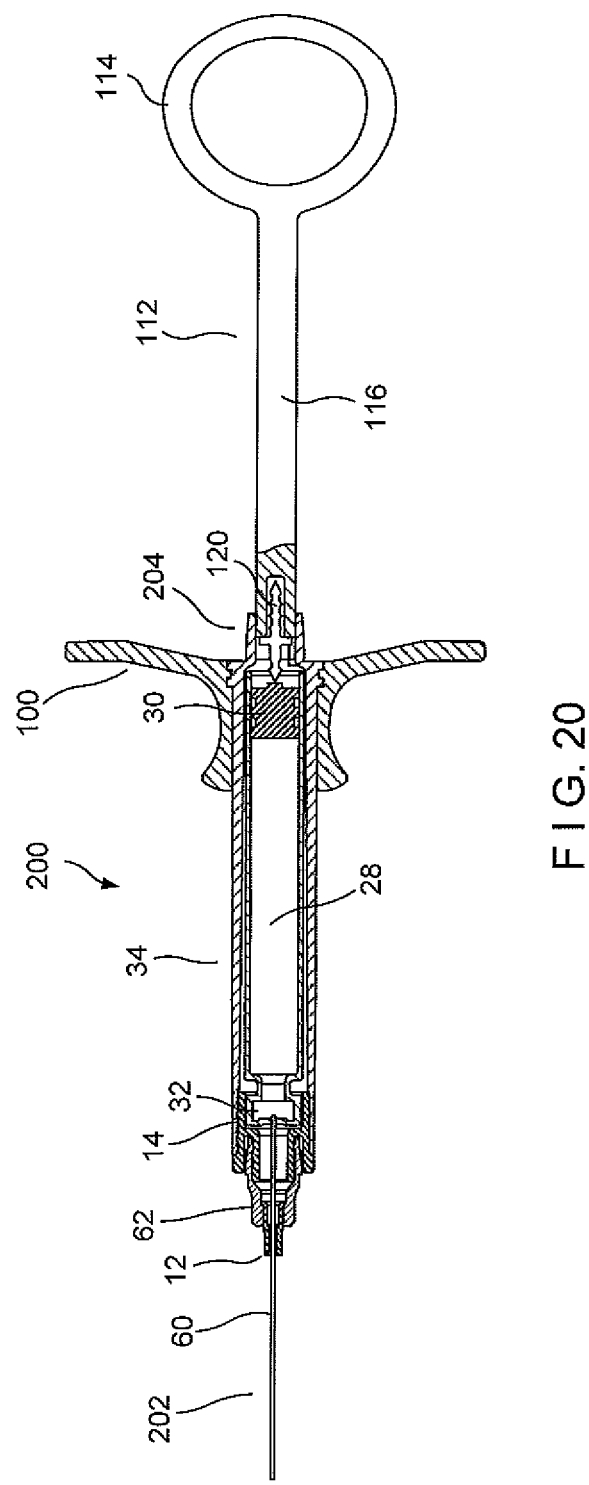
FIG. 20 is a cross-sectional view of an alternative embodiment the assembled injection device of the present disclosure in the armed configuration.

FIGS. 19 and 20 illustrate an alternative embodiment of the injection device 200 of the present disclosure, wherein the housing 34 does not include the mounting hub 93.

Figure 9A:
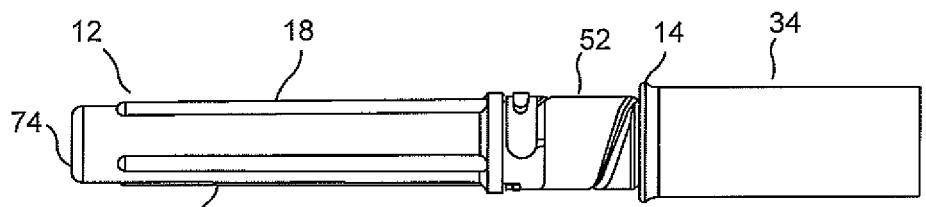
FIG. 9A is a plan view of a portion of the injection device prior to arming of the cartridge, with the peel tab in place, of the present disclosure.
Figure 9B:
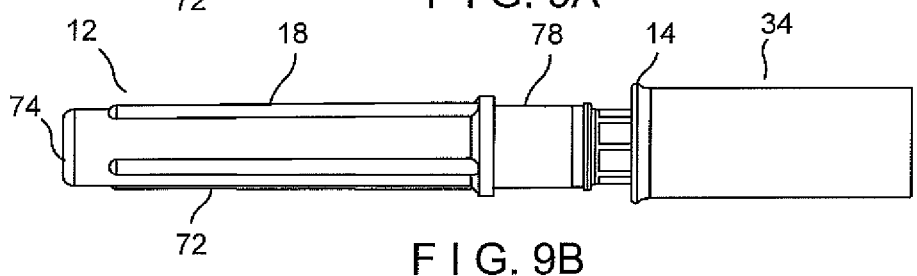
FIG. 9B is a plan view of a portion of the injection device prepared for arming of the injection device, with the peel tab removed, of the present disclosure.
Figure 9C:
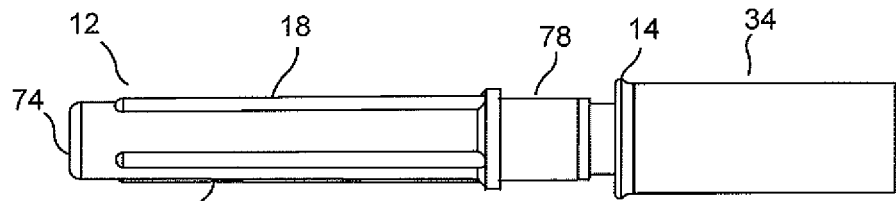
FIG. 9C is a plan view of needle sheath after being moved toward the housing thereby arming the injection device of the present disclosure.
Figure 9D:
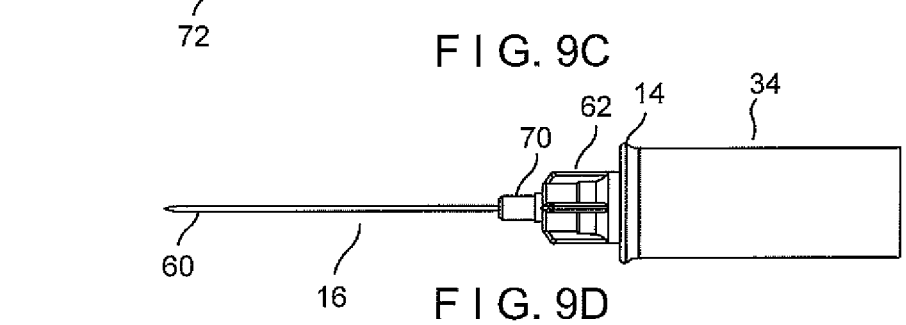
FIG. 9D is a plan view of a portion of the with the needle sheath removed, thereby exposing the needle.
Figure 10A:
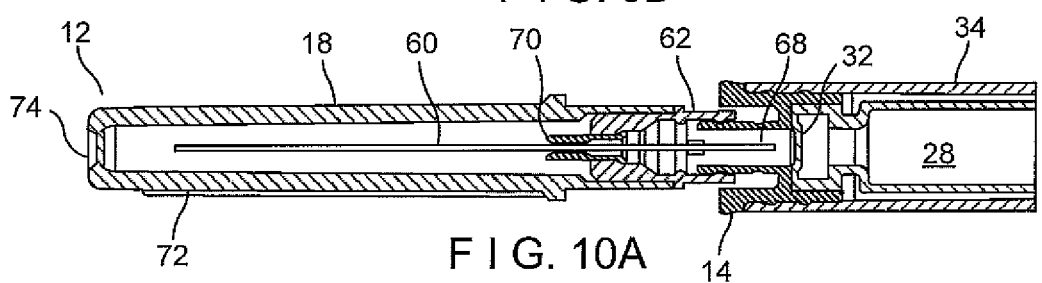
FIG. 10A is a cross-sectional view of a portion of the injection device of the present disclosure, corresponding to FIG. 9B.
Figure 10B:
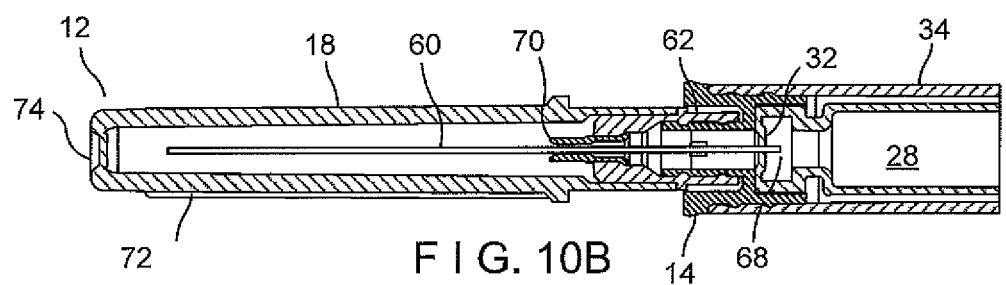
FIG. 10B is a cross-sectional view of a portion of the injection device of the present disclosure, corresponding to FIG. 9C.
Figures 11A, 11B, 11C, 11D:
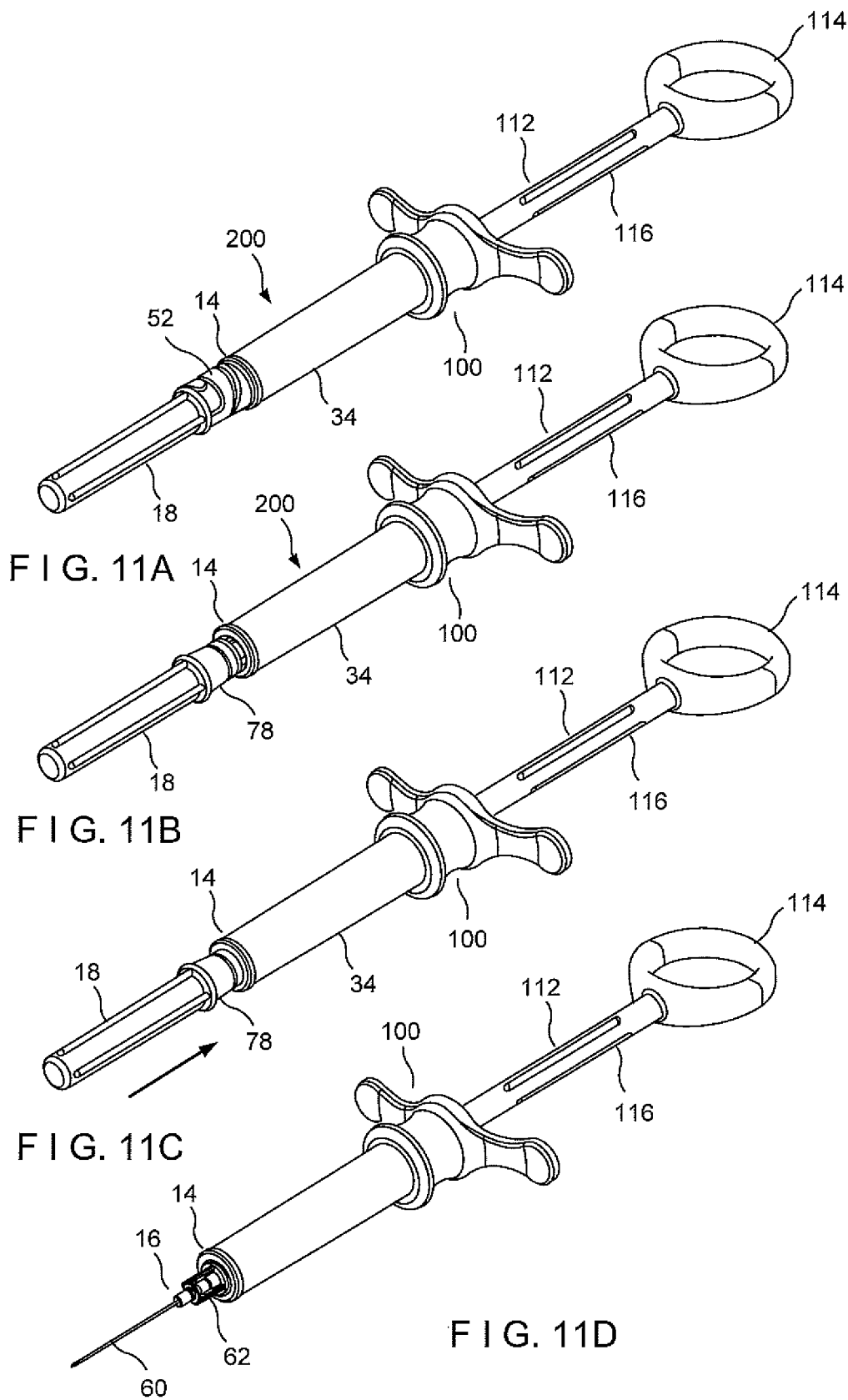
FIG. 11A is a perspective view of the embodiment of the injection device of the present disclosure, corresponding to FIG. 9A.
FIG. 11B is a perspective view of the embodiment of the injection device of the present disclosure, corresponding to FIG. 9B.
FIG. 11C is a perspective view of the embodiment of the injection device of the present disclosure, corresponding to FIG. 9C.
FIG. 11D is a perspective view of the embodiment of the injection device of the present disclosure, corresponding to FIG. 9D.

In order to use injection device 200, the medical professional removes injection device 200 from the package, thereby receiving injection device 200 in the configuration shown in FIGS. 8B and 11A. In some embodiments, the professional may need to insert the plunger rod assembly 112 to the housing after removing the packaging. As previously described, injection device 200 is provided to the professional with the cartridge 28 pre-loaded with the desired drug, pharmaceutical product or other injectable agent. In order to use the injection device 200, the professional must arm the injection device 200 as well as engage the plunger rod assembly 112 to overcome (or disengage) the snap-fit engagement (thereby often producing audible feedback) between the plunger rod assembly 112 and the housing 34 and engage the longitudinally extending harpoon 120 against the cartridge plunger 30 of the cartridge 28. In order to arm the injection device 200, the professional, starting with the first engagement configuration shown in FIGS. 1A, 8C and 9A, grasps the cylindrical peel tab 52 and peels the tab 52 from the injection device 200 thereby reaching the configuration of FIGS. 9B, 10A and 11B (still in the pre-armed or first engagement configuration). The professional then presses the needle sheath 18 toward the housing 34 as shown in FIGS. 9C, 10B and 11C. This relative movement of the needle sheath 18 toward the proximal end 204 of injection device, for example toward the housing 34 causes the interior transverse wall 80 to urge the needle hub 62 toward the housing 34 (i.e., toward the right in FIG. 2, also see arrow in FIG. 11C), this causes the inwardly extending annular ridge 64 to release from the first inwardly extending annular notch 66 on the exterior of the interior cylindrical needle mount wall 50 and, after axially sliding, subsequently engage with the second inwardly extending annular notch 67. In other words, this re-configures the injection device 200 from its first engagement configuration to its second engagement configuration. This likewise drives the butt end 68 of the needle 16 to penetrate the piercable septum 33 of the cap 32 of cartridge 28 thereby providing a sterile fluid path for the injectable agent through cannula 60. The movement of the needle sheath 18 is translated into movement of the needle hub 62 along interior cylindrical mounting wall 50 without being translated to housing 34, thereby allowing housing 34 to stay relatively stationary. Often, audible feedback is generated when the injection device 200 goes from the first engagement or pre-armed position to the second engagement or armed position. The audible feedback provides the medical professional with an indication that the needle 16 is engaged to fully connect the fluid pathway. In this second engagement configuration, the hub 62 of the needle 16 is fully seated within the space 54 formed between circular wall 26 and interior cylindrical needle mount wall 50 of hub-to-cartridge interface 14. The professional then removes the sheath 18 to expose the cannula 60 of the needle 16 as shown in FIGS. 1B, 9D and 11D. The professional is then ready to perform the injection to the patient in the conventional manner.

Figure 16:
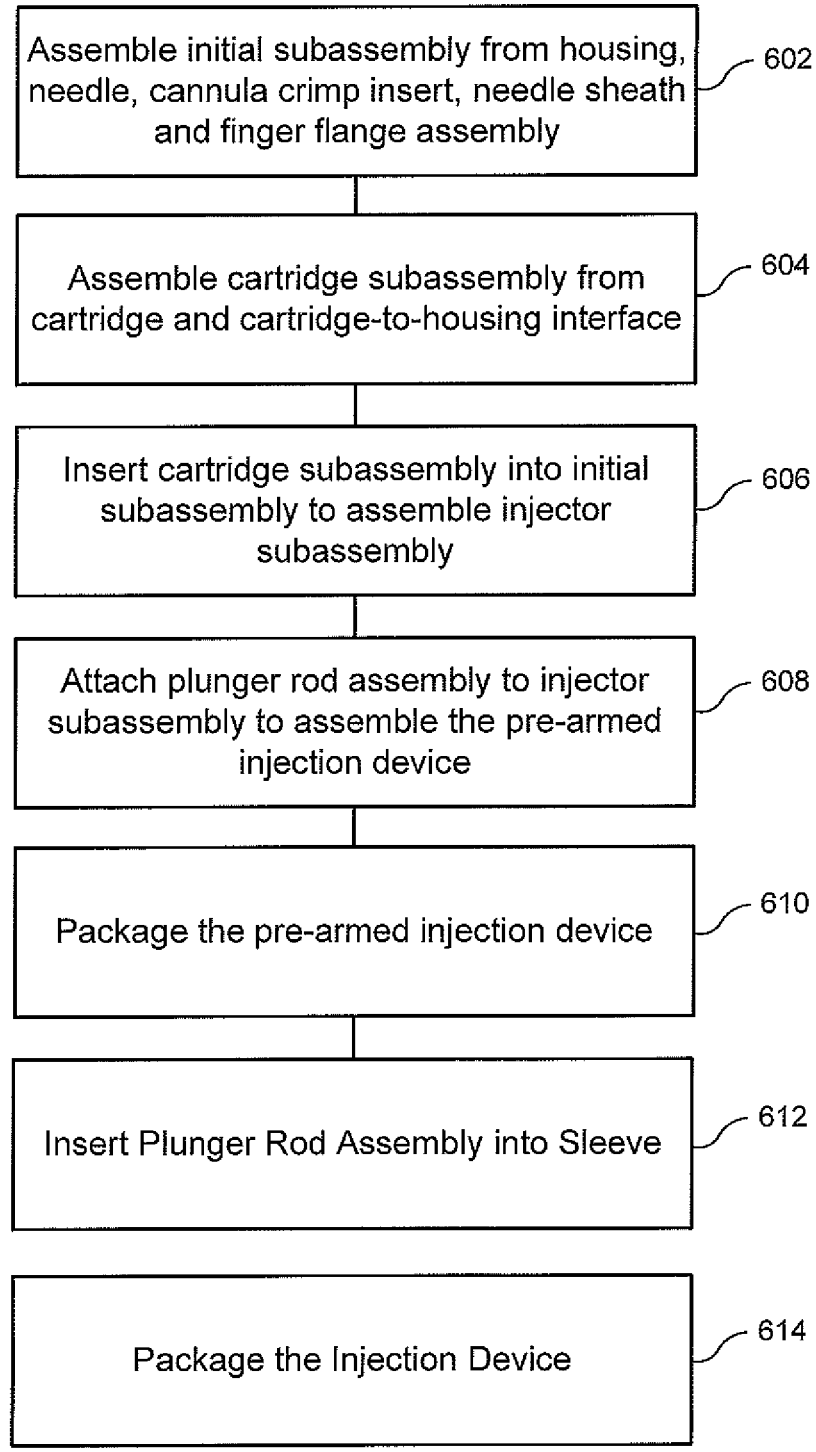
FIG. 16 is a flowchart of the assembly of the injection device of the present disclosure.

FIG. 16 illustrates an exemplary assembly or manufacturing method for injection device 200, but the assembly or manufacture of injection device 200 is not limited thereto. The order of steps presented are merely illustrative and may be performed in a different order or in parallel operations.

In step 602, the needle cannula 60 may be inserted into the needle sheath 18 as shown in FIG. 1D. In step 604, the hub-to-cartridge interface 14 may be attached to the needle 16 and the needle sheath 18 thereby resulting in the needle assembly 12 of FIGS. 1F, 3A and 3B. In step 606, the cartridge 28 may be attached to the hub-to-cartridge interface 14 thereby resulting in the configuration of FIGS. 4B, 5A and 5B. In step 608, the housing 34 may be attached to the hub-to-cartridge interface 14 thereby resulting in the configuration of FIG. 6E. Often, step 608 and subsequent steps do not have a sterility requirement. In other words, steps 608, 610, 612 and 614 often do not have to take place in the previously-described sterile environment. In step 610, the finger flange assembly 100 may be attached to housing 34 thereby resulting in the configuration of FIG. 7D. In step 612, the plunger rod assembly 112 may be attached to mounting hub 93 of housing 34 thereby resulting in the configuration of FIG. 8B. In step 614, the resulting injection device 200 may be packaged.

Thus the several aforementioned objects and advantages are most effectively attained. Although preferred embodiments of the invention have been disclosed and described in detail herein, it should be understood that this invention is in no sense limited thereby and its scope is to be determined by that of the appended claims.

What is claimed is:

1. An injection device comprising:
a cartridge with a first cartridge end and a second cartridge end, the first cartridge end being closed and the second end including a cartridge plunger;
a housing enclosing the cartridge, the housing including a first housing end and a second housing end;
a needle hub holding a needle having a longitudinal axis;
an adapter with a first adapter end and a second adapter end, the first adapter end directly engaging the first cartridge end and the first housing end, and the second adapter end slidably engaging the needle hub, wherein engagement of the second adapter end and the needle hub is movable between a first engagement position and a second engagement position by axial sliding movement of the needle hub relative to the adapter;
wherein in the first engagement position, the needle is spaced away from the first cartridge end and wherein in the second engagement position, the needle penetrates the first cartridge end thereby providing communication of contents of the cartridge to the needle, the first adapter end engaging the first cartridge end and the first housing end when the needle hub is in the first engagement position and when the needle hub is in the second engagement position.

2. The injection device of claim 1 wherein the second adapter end includes a removable tab which engages a first sheath end of a sheath mounted on the adapter and, prior to removal, inhibits movement of the sheath thereby maintaining the injection device in the first engagement position and, after removal, permits movement of the sheath to urge the injection device from the first engagement position to the second engagement position.

3. The injection device of claim 2 wherein the removable tab wraps around the first sheath end and is comprised of low density polyethylene.

4. The injection device of claim 1 wherein the second adapter end includes a first cylindrical wall for engaging the needle hub, the first cylindrical wall including a first detent element and a second detent element, and wherein the needle hub includes a hub detent element, wherein the first configuration is a first detent configuration wherein the hub detent element engages the first detent element and wherein the second configuration is a second detent configuration wherein the hub detent element engages the second detent element.

5. The injection device of claim 4 wherein the first and second detent elements are respective first and second annular grooves formed on the first cylindrical wall.

6. The injection device of claim 5 wherein the hub includes an interior cylindrical hub wall which is concentrically outward from the first cylindrical wall of the second adapter end, and wherein the hub detent element is an annular ridge.

7. The injection device of claim 6 wherein the first adapter end includes a second cylindrical wall, wherein the cartridge is engaged within an interior of the second cylindrical wall and the housing is detent engaged by an exterior of the second cylindrical wall.

8. The injection device of claim 7 wherein at least a portion of the second cylindrical wall is outwardly concentric from at least a portion of the first cylindrical wall.

9. The injection device of claim 8 wherein a space is formed between the first cylindrical wall and the second cylindrical wall, and wherein, in the second detent configuration, the needle hub is seated within the space.

10. The injection device of claim 4 further including a sheath covering the needle, the sheath including a first sheath end and a second sheath end, wherein the first sheath end is open and is engaged by the second adapter end.

11. The injection device of claim 10 wherein the second sheath end is closed.

12. The injection device of claim 10 wherein the sheath includes a hub engagement element for engaging the hub, whereby manual force on the sheath can urge the injection device from the first detent configuration to the second detent configuration.

13. The injection device of claim 12 wherein the hub engagement element is a transverse wall within the sheath, the transverse wall including a passageway through which a portion of the needle extends.

14. The injection device of claim 10 further including a plunger rod assembly extending through the second housing end, for engagement with the cartridge plunger.

15. The injection device of claim 14 wherein the plunger rod assembly includes a plunger detent element for engaging the second housing end, thereby holding the plunger rod assembly in place prior to engagement with the cartridge plunger.

16. The injection device of claim 15 wherein the plunger detent element provides a snap detent engagement between the plunger rod and the second housing end, whereby user operation of the plunger rod builds up force prior to release of the snap detent element thereby increasing a velocity of the plunger rod.

17. The injection device of claim 15 wherein disengagement of the plunger detent element produces audible feedback.

18. The injection device of claim 15 wherein disengagement of the plunger detent element produces tactile feedback.

19. The injection device of claim 14 further including a radially extending finger flange assembly proximate to the second housing end.

20. The injection device of claim 19 wherein the finger flange assembly is rotatable with respect to the housing.

21. The injection device of claim 1 wherein the first cartridge end is closed by a metal cap.

22. The injection device of claim 21 wherein the cartridge includes a drug or pharmaceutical product.

23. The injection device of claim 1 wherein the first housing end extends distally past the first cartridge end.

24. The injection device of claim 1 wherein an inner surface of the housing engages an outer surface of the adapter.

25. The injection device of claim 1 wherein the adapter is detent engaged with the housing in the first and second engagement positions.

26. An injection device comprising:
a cartridge with a first cartridge end and a second cartridge end, the first cartridge end being closed and the second end including a cartridge plunger;
a housing enclosing the cartridge, the housing including a first housing end and a second housing end, the first housing end extending distally past the first cartridge end;
a needle hub holding a needle;
an adapter with a first adapter end and a second adapter end, the first adapter end directly engaging the first cartridge end and the first housing end, and the second adapter end slidably engaging the needle hub, wherein engagement of the second adapter end and the needle hub is movable between a first engagement position and a second engagement position;
wherein in the first engagement position, the needle is spaced away from the first cartridge end and wherein in the second engagement position, the needle penetrates the first cartridge end thereby providing communication of contents of the cartridge to the needle, the second adapter end including a first cylindrical wall for engaging the needle hub, the first cylindrical wall including a first detent element and a second detent element, and wherein the needle hub includes a hub detent element, wherein the first engagement position is a first detent configuration wherein the hub detent element engages the first detent element and wherein the second engagement position is a second detent configuration wherein the hub detent element engages the second detent element, and wherein the first and second detent elements are respective first and second annular grooves formed on the first cylindrical wall, the hub including an interior cylindrical hub wall which is concentrically outward from the first cylindrical wall of the second adapter end, and wherein the hub detent element is an annular ridge, the adapter securing the first cartridge end in a designated position relative to the first housing end when the needle hub is in the first engagement position, and the adapter securing the first cartridge end in the designated position relative to the first housing end when the needle hub is in the second engagement position.

27. The injection device of claim 26 wherein an inner surface of the housing engages an outer surface of the adapter.

28. An injection device comprising:
a cartridge with a first cartridge end and a second cartridge end, the first cartridge end being closed and the second end including a cartridge plunger;
a housing enclosing the cartridge, the housing including a first housing end and a second housing end, the first housing end extending distally past the first cartridge end;
a needle hub holding a needle;
an adapter with a first adapter end and a second adapter end, the first adapter end directly engaging the first cartridge end and the first housing end, and the second adapter end slidably engaging the needle hub, wherein engagement of the second adapter end and the needle hub is movable between a first engagement position and a second engagement position, wherein in the first engagement position, the needle is spaced away from the first cartridge end and wherein in the second engagement position, the needle penetrates the first cartridge end thereby providing communication of contents of the cartridge to the needle, and wherein the second adapter end includes a first cylindrical wall for engaging the needle hub, the first cylindrical wall including a first detent element and a second detent element, and wherein the needle hub includes a hub detent element, wherein the first configuration is a first detent configuration wherein the hub detent element engages the first detent element and wherein the second configuration is a second detent configuration wherein the hub detent element engages the second detent element, the adapter securing the first cartridge end in a designated position relative to the first housing end when the needle hub is in the first engagement position, and the adapter securing the first cartridge end in the designated position relative to the first housing end when the needle hub is in the second engagement position; and
a sheath covering the needle, the sheath including a first sheath end and a second sheath end, wherein the first sheath end is open and is engaged by the second adapter end, wherein the sheath includes a hub engagement element for engaging the needle hub, whereby manual force on the sheath can urge the injection device from the first detent configuration to the second detent configuration, wherein the hub engagement element is a transverse wall within the sheath, the transverse wall including a passageway through which a portion of the needle extends.

29. The injection device of claim 28 wherein an inner surface of the housing engages an outer surface of the adapter.

* * * * *